US011542516B2

(12) United States Patent
Flasinski et al.

(10) Patent No.: US 11,542,516 B2
(45) Date of Patent: Jan. 3, 2023

(54) PLANT REGULATORY ELEMENTS AND USES THEREOF

(71) Applicant: MONSANTO TECHNOLOGY LLC, St. Louis, MO (US)

(72) Inventors: Stanislaw Flasinski, Ballwin, MO (US); Jun Zhang, O'Fallon, MO (US); Suling Zhao, St. Charles, MO (US)

(73) Assignee: MONSANTO TECHNOLOGY, LLC, St. Louis, MO (US)

( * ) Notice: Subject to any disclaimer, the term of this patent is extended or adjusted under 35 U.S.C. 154(b) by 438 days.

(21) Appl. No.: 16/540,183

(22) Filed: Aug. 14, 2019

(65) Prior Publication Data

US 2020/0063150 A1   Feb. 27, 2020

Related U.S. Application Data

(62) Division of application No. 15/449,534, filed on Mar. 3, 2017, now Pat. No. 10,421,974, which is a division of application No. 14/207,302, filed on Mar. 12, 2014, now Pat. No. 9,617,553.

(60) Provisional application No. 61/785,245, filed on Mar. 14, 2013.

(51) Int. Cl.
  *C12N 15/82* (2006.01)
  *C07K 14/415* (2006.01)

(52) U.S. Cl.
  CPC ........ *C12N 15/8216* (2013.01); *C07K 14/415* (2013.01); *C12N 15/8212* (2013.01); *C12N 15/8225* (2013.01); *C12N 15/8227* (2013.01); *C12N 15/8241* (2013.01); *C12N 15/8274* (2013.01); *C12N 15/8279* (2013.01)

(58) Field of Classification Search
  None
  See application file for complete search history.

(56) References Cited

U.S. PATENT DOCUMENTS

| 7,547,774 | B2 | 6/2009 | Flasinski et al. |
| 2006/0101541 | A1 | 5/2006 | Flasinski et al. |
| 2006/0218662 | A1 | 9/2006 | Hammer |
| 2007/0130645 | A1 | 6/2007 | Wu et al. |
| 2007/0209085 | A1 | 9/2007 | Wu et al. |
| 2009/0293154 | A1 | 11/2009 | Yelin et al. |
| 2011/0078833 | A1* | 3/2011 | Wu ................... C12N 15/8229 435/417 |
| 2012/0210463 | A1 | 8/2012 | Diehn et al. |
| 2014/0109261 | A1 | 4/2014 | Flasinski et al. |

FOREIGN PATENT DOCUMENTS

| CN | 1310760 A | 8/2001 |
| CN | 102686605 | 9/2012 |
| JP | 2002-533057 | 10/2002 |
| RU | 2197527 | 1/2003 |
| WO | WO 1996/007746 | 3/1996 |
| WO | WO 1999/058659 | 11/1999 |
| WO | WO 2007/049275 | 5/2007 |
| WO | WO 2009/126470 | 10/2009 |
| WO | 2011088299 A1 | 7/2011 |
| WO | WO 2012/112411 | 8/2012 |
| WO | WO 2012/158535 | 11/2012 |

OTHER PUBLICATIONS

Benfey and Chua, 1990, The Cauliflower Mosaic Virus 35S Promoter: Combinatorial Regulation of Transcription in Plants, Science 250: 959-966.*
Morton et al., 2014, Paired-End Analysis of Transcription Start Sites in *Arabidopsis* Reveals Plant-Specific Promoter Signatures, The Plant Cell 26: 2746-2760 .*
Dutt et al., 2014, Temporal and spatial control of gene expression in horticultural crops, Horticulture Research 1, 14047: 1-17.*
Mignone et al., 2011, mRNA Untranslated Regions (UTRs), In: eLS, John Wiley & Sons, Ltd: Chichester, pp. 1-5.*
Rombauts et al., 1999, PlantCARE, a plant cis-acting regulatory element database, Nucleic Acid Research 27: 295-296.*
Benfey et al., "The CaMV 35S enhancer contains at least two domains which can confer different developmental and tissue-specific expression patterns," *EMBO J* 8(8):2195-2202, 1989.
Cho et al., "Regulation of root hair initiation and expansin gene expression in *Arabidopsis*," *Plant Cell* 14:3237-3253, 2002.
Gilissen et al., "Biosafety of *E. coli* beta-glucuronidase (GUS) in plants," *Transgenic Research* 7:157-163, 1998.
Iwase et al., "Manipulation of plant metabolism by transcription factors," *Plant Biotechnology* 26:29-38, 2009.
Kim et al., "A 20 nucleotide upstream element is essential for the nopaline synthase (nos) promoter activity," *Plant Mol Biol* 24(1):105-117, 1994.
Odell et al., "Identification of DNA sequences required for activity of the cauliflower mosaic virus 35S promoter," *Nature* 313:810-812, 1985.
Piechulla et al., "Identification of tomato Lhc promoter regions necessary for circadian expression," *Plant Molec Biol* 38(4):655-662, 1998.
Sherf et al., "Dual-Luciferase™ Reporter Assay: An Advanced Co-Reporter Technology Integratign Firefly and *Renilla* Luciferase Assays," *Promega Notes Magazine* No. 57:2, 1996.

(Continued)

*Primary Examiner* — Weihua Fan
*Assistant Examiner* — Brian James Sullivan
(74) *Attorney, Agent, or Firm* — Dentons US LLP; Judith Koehler

(57) ABSTRACT

Recombinant DNA molecules and constructs including sequences derived from *Tripsacum dactyloides* are provided, which are useful for modulating gene expression in plants. Transgenic plants, plant cells, plant parts, and seeds are also provided, comprising a recombinant DNA molecule operably linked to a heterologous transcribable DNA molecule, as well as methods of their use.

16 Claims, 3 Drawing Sheets

Specification includes a Sequence Listing.

(56) References Cited

OTHER PUBLICATIONS

Wei et al., "Comparative expression analysis of two sugarcane polyubiquitin promoters and flanking sequences in transgenic plants," *Journal of Plant Physiology* 160:1241-1251, 2003.
Welsch et al., "Structural and functional characterization of the phytoene synthase promoter from *Arabidopsis thaliana*," *Planta* 216:523-534, 2003.
Elmayan et al., "Synthesis of a bifunctional metallothionein/β-glucuronidase fusion protein in transgenic tobacco plants as a means of reducing leaf cadmium levels," *The Plant Journal* 6(3):433-440, 1994.
International Search Report and Written Opinion regarding International Application No. PCT/US2014/024511, dated Jun. 23, 2014.
Jeong et al., "Root-Specific Expression of OsNAC10 Improves Drought Tolerance and Grain Yield in Rice under Field Drought Conditions," *Plant Physiology* 153:185-197, 2010.
Kinkema et al.," An improved chemically inducible gene switch that functions in the monocotyledonous plant sugar cane," *Plant Molecular Biology* 84:443-454, 2013.
Vettore et al., "The libraries that made SUCEST," *Genetics and Molecular Biology* 24(1-4):1-7, 2001.
Written Opinion of the International Preliminary Examining Authority regarding International Application No. PCT/US2014/024511, dated Mar. 27, 2015.
Xiong et al., "Concurrent mutations in six amino acids in β-glucuronidase improve its thermostability," *Protein Engineering, Designs Selection* 20(7):319-325, 2007.
Redillas et al., "The use of JIP test to evaluate drought-tolerance to transgenic rice overexpressing OsNAC10," *Plant Biotechnol. Rep.* 5:169-175, 2011.
Office Action regarding Chinese Application No. 2014800267082, dated Jul. 19, 2016.
Supplementary European Search Report regarding European Application No. 14774111.0, dated Oct. 21, 2016.
EBI Accession No. CG049384, dated Aug. 28, 2003.
EBI Accession No. DX337374, dated Jan. 22, 2006.
Xu et al., "Characterization of a Rice Gene Family Encoding Root-Specific Proteins," *Plant Molecular Biology* 27(2):237-248, 1995.
Dutt et al., "Temporal and spatial control of gene expression in horticultural crops," *Horticulture Research* 1 14047:1-17, 2014.
Morton et al., "Paired-End Analysis of Transcription Start Sites in *Arabidopsis* Reveals Plant-Specific Promoter Signatures," *The Plant Cell* 26:2746-2760, 2014.

Benfey et al., "The Cauliflower Mosaic Virus 35S Promoter: Combinatorial Regulation of Transcription in Plants," *Science* 250:959-966, 1990.
European Extended Search Report regarding European Application No. 14774111, dated Feb. 28, 2017.
Office Action regarding Colombian Application No. 15243183, dated Jun. 12, 2017.
Tanaka et al., "Enhancement of foreign gene expression by a dicot intron in rice but not in tobacco is correlated with an increased level of mRNA and an efficient splicing of the intron," *Nucleic Acids Research* 18(23): 6767-6770, 1990.
Xiong et al., "A thermostable β-Glucuronidase Obtained by Directed Evolution as a Reporter Gene in Transgenic Plants," *PLOS One* 6(11):e26773 , 2011.
Lin et al., "Molecular Cloning, Mass Spectrometric Identification, and Nutritional Evaluation of 10 Coixins in Adlay (*Coix lachryma-jobi* L.)," *J. Argic. Food Chem.* 57:10916-10921, 2009.
Lu et al., "Characterization of Oil Bodies in Adlay (*Coix lachryma-jobi* L)," *Biosci. Biotechnol. Biochem*. 74(9):1841-1847, 2010.
Yoza et al., "Molecular Cloning and Functional Expression of cDNA Encoding a Cysteine Proteinase Inhibitor, Cystatin, from Job's Tears (*Coix lacryma-jobi* L. var. *Ma-yuen* Stapf)," *Biosci. Biotechnol. Biochem.* 66(10):2287-2291, 2002.
Russian Office Action regarding Russian Application No. 2015143455, dated Dec. 25, 2017.
Donald et al., "Mutation of either G box or I box sequences profoundly affects expression from the *Arabidopsis* rbcS-1A promoter," *The EMBO Journal* 9(6):1717-1726, 1990.
Singer et al., *Genes and Genomes*, Moscow, Mir, 1998, vol. 1, pp. 63-64.
Office Action for corresponding Chile Patent Application No. 201801366, dated Jun. 17, 2019, 19 pages.
Office Action for corresponding Chile Patent Application No. 201801365, dated Jun. 17, 2019, 21 pages.
Rombauts et al., Nucleic Acid Research 27:295-296 (1999).
Mignone et al., In: eLS, John Wiley & Sons, Ltd., Chichester, pp. 1-5 (2011).
Extended European Search Report regarding Europe Application No. 19197938 dated Dec. 3, 2019.
EBI Accession No. CA132556, Sep. 25, 2003.
Extended European Search Report regarding Europe Application No. 19197949 dated Jan. 13, 2020.
EBI Accession No. GS070593, Aug. 10, 2009.
Extended European Search Report regarding Europe Application No. 19197957 dated Jan. 13, 2020.
EBI Accession No. CW327880, Nov. 1, 2004.

* cited by examiner

FIG. 1a

```
CR-Ec.uidA_nno-1:1:1      CAGCAAGTCGTGCCACGGCCAGGGCACCAGCGGCACCCTCCAAGTCGTCAACCCTCAC
CR-Ec.uidA-1:1:4          CAACAGGTGGTTGCAACTGGACAAGGCACTAGCGGGACTTTGCAAGTGGTGAATCCGCAC
                          ** ** ******* ** ****** ****** ******  ** ** ** **  ******

CR-Ec.uidA_nno-1:1:1      CTCTGGCCAGCCTGGCGAGGGCTACCTCTACGAGCTGTGCGTCACCGCCAAGAGCCAGACT
CR-Ec.uidA-1:1:4          CTCTGGCAACCGGGTGAAGGTTATCTCTATGAACTGTGCGTCACAGCCAAAAGCCAGACA
                          *******  ** *  ** ** ** ***** ** ********** ****** ********

CR-Ec.uidA_nno-1:1:1      GAGTGCGACATCTACCCTCTCCGCGTCGGCATCAGGAGCGTCGCTGTCAAGGGCGAGCAG
CR-Ec.uidA-1:1:4          GAGTGTGATATCTACCCGCTTCGCGTCGGCATCCGGTCAGTGGCAGTGAAGGGCGAACAG
                          *****   ********* ** ************ ** ***  ** ****** ** ***

CR-Ec.uidA_nno-1:1:1      TTCCTCATCAACCACAAGCCTTTCTACTTCACTGGTTTCGGCCCGCCACGAGGACGCTGAC
CR-Ec.uidA-1:1:4          TTCCTGATTAACCACAAACCGTTCTACTTTACTGGCTTTGGTGTCGTCATGAAGATGCGAC
                          ***** ** ******** ** ******** ****  *** **  *** ** ** ** **

CR-Ec.uidA_nno-1:1:1      CTGAGGGGCAAGGGTTTCGACAACGTCCTGATGGTCCACGACACGCTCTGATGGACTGG
CR-Ec.uidA-1:1:4          TTGCGTGCAAAGGATTCGATAACGTGCTGATGGTGCACGACCACCAGCATTAATGGACTGG
                          * * *  ****** ***** *****  ******* ******  *  **   *********

CR-Ec.uidA_nno-1:1:1      ATCGGTGCCAACAGCTACAGGACCAGTCACTCACCCGTACGCTGAGGAGAGATGCTGGACTGG
CR-Ec.uidA-1:1:4          ATTGGGGCCAACTCCTACCGTACGCTTACCCTTACCCTACGCTGAAGAGATGCTCGACTGG
                          ** ** ******  **** **** ***** ****  * ********* ***** ******

CR-Ec.uidA_nno-1:1:1      GCTGACGAGCACGGTATCGTCGTGATCGACGAGACTGCTGCGGTCGGTTTCAACCTGTCT
CR-Ec.uidA-1:1:4          GCAGATGAACATGGCCATCGTGGTTGATTGATGAAAACTGCTGTGTCGGCTTTAACCTCTCT
                          ** ** ** ** **  ***** ** **  ** ** * ***** * ***  ** ***** **

CR-Ec.uidA_nno-1:1:1      CTGGGCATTGGTTTCGAGGCTGGGAACAAGCCGAAGGAGCTGTACTCTGAGGAAGCTGTC
CR-Ec.uidA-1:1:4          TTAGGCATTGGTTTCGAAGCGCAACAAGCCGAAAGAAGCGATTACAGCGAAGAGGCAGTC
                          * ************** **    ** ********* **  * **  ** ** **  ***

CR-Ec.uidA_nno-1:1:1      AACGGCGAGACTCCGTCTGTCGTGATGTGGCTTATTGCGAATGAGCCGGACACCAGCAAGG
CR-Ec.uidA-1:1:4          AACGGGGAAACTCAGCAAGCGCACTTACAGCGCACTACAGCGCACTGATAGAGCCAGGACAAG
                          ***** ** **** *  ** *** * *** ** *** ***  ***   ** *****

CR-Ec.uidA_nno-1:1:1      AACCATCCGTCTGTCGTGATGTGTCTATTGCGAAATGAGCCGGACACCGACCGCAAGGG
CR-Ec.uidA-1:1:4          AACCACCCAAGCGTGTGATGTGAGTATTGCCAAGAACCGGATACCCGTCCGCAAGGT
                          *****  *  ** ** *** ***  ****** **  **** *** * *****  *

CR-Ec.uidA_nno-1:1:1      GCGCGTGAATACTTCGCGCCGCTGGCGAGGCGACTCGCAAACTGACCCAACCCGTCCA
CR-Ec.uidA-1:1:4          GCACGGGAATATTTCGCCCCACTGGCGAAGCAACGCCGTAAACTCGACCCGACCCGTCCG
                          **  * ***** ***** **  ******  ** *  *   **** *****   ****** 
```

FIG. 1b

```
CR-Ec.uidA_nno-1:1:1    ATCACGTGCGTCAATGTCATGTGTTCTGCGACGCCCATACGGATATACGATCTCGGACCTGTTC
CR-Ec.uidA-1:1:4        ATCACCTGCGTCAATGTAATGTTCTGCGACGTCACACCGATACCATCAGCGATCTCTTT
                        ***** *** ********** ******************** ** ** ****** ***  ** ** **

CR-Ec.uidA_nno-1:1:1    GATGTTCTTTGTCTCAATCGGTACTATGGGTGGTATGTTCAGAGCGGGGATCTTGAGACG
CR-Ec.uidA-1:1:4        GATGTGCTGTGCCTGAACCGTTATTACGGATATGTGTGATTTCCAAAGCGGCGATTTGGAAACG
                        ***** *** *  **  *** ** **  * ***** *** *** ** *** ***  ** ***

CR-Ec.uidA_nno-1:1:1    GCGGAGAAGGTTCTTGAGAAGGAACTCCTGGCGTGGCAAGAGAAGCTCCATCAGCCGATC
CR-Ec.uidA-1:1:4        GCAGAGAAGGTACTGGAAAAGAACTTCTGGCCTGGCAGGAGAAACTGCATCAGCCGATT
                        ** ******** ** *** ***** ******* **** ****** * **********

CR-Ec.uidA_nno-1:1:1    ATTATCACGGAGTACGGGGTTGACACACTTGCGGGCCTTCACAGTATGTACACAGATATG
CR-Ec.uidA-1:1:4        ATCATCACCGAATACGGCGTCGATACGCTTAGCGGGCTTGCACTCAATGTACACCGACATG
                        ** ***** ** ***** **  *  ** ** ** *  **  * *  **  ****** ** ***

CR-Ec.uidA_nno-1:1:1    TGGTCGGAGGAATACCAGTGTGCCATGGTTGGATATATGTACCATCGTGTCTTCGACCGGGTT
CR-Ec.uidA-1:1:4        TGGAGTGAAGAGTATCAGTGTGCATGGCTGATGTGCTGATATGTATCACCGCGTCTTTGATCGCGTC
                        ***  * ** ** ** ******** *** *** ****  *  ** **  *** * ** ****

CR-Ec.uidA_nno-1:1:1    TCAGCGGTTGTCGGCGAACAAGTCTGGAACTTCGCAGACTTCGCCACGAGCCAAGGGATA
CR-Ec.uidA-1:1:4        AGCGCCCGTCGTCGGTGAACAGTATGGAATTTCGCCGATTTTGCCACCTCGCAAGGCATA
                          *  ** ** ** **  ****  * *****  *****   **  ** ****  ** ****

CR-Ec.uidA_nno-1:1:1    CTGCGGGTAGGAGGGAACAAGAAGGAATCTTCACACGGATCGGAAGCCCAAGTCAGCA
CR-Ec.uidA-1:1:4        TTGCGCGTTGGCGTTGGCGGTAACAAGAAAAGGGATCTTCACTCGCCGACCGCAAACCGAAGTCGGCG
                        ****  ** ** *   ** ******** ** **** ***** ** ** ** ******  ***

CR-Ec.uidA_nno-1:1:1    GCCTTCCTGTTGCAGAAGCGATGACAGGAATGAACTTCGGAGAAAAGCCACAGCAAGGC
CR-Ec.uidA-1:1:4        GCTTTTCTGCTGCAAAAACGCTGGACTGGCATGACTGGACTTCGGTGAAAAACCGCAGCAGGGA
                        ** ** *** **** ** ** *** ** ****  ****** ***** ** **** ****

CR-Ec.uidA_nno-1:1:1    GGAAAGCAGTGA
CR-Ec.uidA-1:1:4        GGCAAACAATGA
                        ** *** ** ***
```

FIG. 1c

SEQUENCE LISTING

<160> NUMBER OF SEQ ID NOS: 44

<210> SEQ ID NO 1
<211> LENGTH: 1500
<212> TYPE: DNA
<213> ORGANISM: Coix lacryma-jobi

<400> SEQUENCE: 1

```
gttgacgtcg gaagtgatcc gaatcaaaca ccaacagggc tagaacgccc ggagagcgag      60
gttgcagttc aacctgctga gacagcaggg accctggcta aaccgacgaa aaccgatcta     120
gagaccggtt tagatcgatc tagggtttcg ggctcctgtg ttgataactc tagaactcct     180
cccgggaaga cccgtagggg agaagcacgt agaggttgtc ctaggaccag caaggccgcc     240
tagaacgccg tcaagtctcg tcgggagacg cgccgaacag caaggtagaa ggaaaaaggg     300
gtaaaagggt agtagattga ttttgatcga ttagggtcgg atgcctcaat cggccatgat     360
cctctcatat atatagaggg ggctggtctt atcccaatag gaaacatctc cggatacgat     420
ctccaagctt cctatccgga ctctatcaac atatagaatt caatccggac gtgacaaggt     480
aaccctgatt tcgccgatcc ttggatcgac cagatcggtc taatgggctt tatcagccca     540
tactgatcaa caaatcgtcc ttacaagaga aggatccaca tacttagcgt cggactcagc     600
aatcatcaca accataaggc ctccaaccag ggccacctgg tcggacataa catgagtgat     660
cggaaaccca aaatgatcag gcccattcaa cttagaacat ctgatctctc aaaagacaaa     720
ttcgacctta atattacagg ccgaatactt cttctaaatt cattttatc tgtgacactt      780 ttgagtgtca acagtatgct tttctttgca aatattccct ttttatttc tacccattag      840 ttactttggc ccttccattt cattgtatgt aaaagtggat actaaagcta acgcaacaag     900
aacaaaaata aatgatccg gggtatgacg tccccacgga tatttacta aaatatcttc       960 tcatcagatc tagaaaatcc tcgggcccta tccatatagg gtggtatcac atccatatac    1020
ttatagtagg acagatgagg agattttttt accctcaatt ctaaaattca tcactttaat    1080
taaaggaatt taactcagga ccagagcggt gtcgcgagag ccatatatgt aaccaaaata    1140
cctattagtt tagggcagca gcaaataaac cattattcct ttgtcccctt attccgtctc    1200
cagctagcta aaagctgtac atatgattaa tcatcgacat cgtgcatgca atttgcagga    1260
```

```
aagtgcaagg agcagccagg tgtatacacg tctgtagggt tcgcgtcaca tcgatcacat    1320
ggatatgcat gcatccaaaa cacacgtacg tacacttgct ggtgcatgcc ttatgaaatg    1380
gaatactaca cgcatgtcca caagttaagc acgcacaggc acacacacag agagacacag    1440
ttgctcgctc aatgcaattg ctggtctcat aaataccacc gaagagaacc atcctaaaga   1500

<210> SEQ ID NO 2
<211> LENGTH: 86
<212> TYPE: DNA
<213> ORGANISM: Coix lacryma-jobi

<400> SEQUENCE: 2
acacaccggt agcgattcga tccttcagaa gagctactgc tagctagcta gagctatcat      60
ctgatcggta gcagcaatat aattca                                          86

<210> SEQ ID NO 3
<211> LENGTH: 594
<212> TYPE: DNA
<213> ORGANISM: Digitaria sanguinalis (L.) Scop.

<400> SEQUENCE: 3
accaacaagc atcatgacaa tggcagcaaa gcattcgtca gagacgacca acaagcatca      60
cgacactggc ggcaaagcat atcaaaacaa tgtaatgaga tacaatattg tttcataaag    120
aagcctacct gcatgatcct ttctaacaaa ctcaaaatga taagggccat gctctgttcg    180
gtgacaacct tcaaggcatc tactttgcca gaatttagct tgttattac cagcttgtta    240 ttagttctta ctatccagtc tcgaacaact tgggcgccct tgtctcatc ataccctctac     300 atactgccct ccctgatcaa cacaacattc ttcaacccaa tcccttggca tttgcgcatg    360
ttacaaggtg caaaacagcc agcccatatt gcaagttact aaactaaact atggtccaaa    420
tgcagcaatc ttgatcgcta gtactgtccg gcattatatc tgaaacaagt ccagatcacc    480
catctcatca cagtcacatg cattcgcgtt cacggaaacc gttaacacac caccaactag    540
tcagcattgc accaatcttc ctccctataa atgcagcaac aatcgagcga cacc          594

<210> SEQ ID NO 4
<211> LENGTH: 88
<212> TYPE: DNA
<213> ORGANISM: Digitaria sanguinalis (L.) Scop.

<400> SEQUENCE: 4
aacaccacga accatcacag gcacttatag caacaatcaa gttatttctg ccttgtgcac       60
tcgtggtcga gtagtaatac atagcaaa                                         88

<210> SEQ ID NO 5
<211> LENGTH: 1500
<212> TYPE: DNA
<213> ORGANISM: Digitaria sanguinalis (L.) Scop.

<400> SEQUENCE: 5
ttgccggcct gtgtgatgtt gcgcccccac caacctttga ttttgcctgc tgccttgtca       60
gccaacggtt ggtagtccac cctcttcaaa cgtcgcaccg aagttctgtc gactcccaga     120
gaaaatattg tatgtaacat atactattac tactacagct gaacacgtaa caatatgatc     180
ttatttgtgt atgccgaaag caccgtgcta aagaccacct atcgccctgg ttgggatcga     240
ggccttgctg ctcagccggt tgcatcagac gtgtgcgtgc atcgcatgac tggcatgtga     300
```

```
gttgtggttc ataaataatg tctaacaata ttaaggtaat tcctagtatg cgttgggatc    360 atttttttgat gttggatctt gcggcaggtc tcacccatgc atgacggatt gagaacaagg    420
gagactggac cagcatgtaa aagataatga tgaaggcgag ccatgttgac ggtgtaccgg    480
gacaggcaga cgcgggccaa catcgaagag ggagatagcg tgcgtgctaa tgttttttgtg    540 gctcgcatgt tcaatgactc atacagattt cggtagcttg ctaaaatcat tcagcttgtc    600
ggcaagcatg ggccaaacaa tctagcaaca atccatgttt gccatcgatg caataggaag    660
taatagaatc cacttagctt ctagatctca cctggatcct ccttttattt atatgcatat    720
attttgtggt agtggaggca cacatcttta tgtttcatgg ataatatttt gttatatgta    780
tatctgtcca aataaataac gtacgtgtcc ttcaatctta gactccagtt agattgatca    840
atgtagtggt cttccatatt cctttttgtgt tttgtgtgcc atgtctcaag catgcatgtg    900
gaatgaaaag ctggaagctt ggcatcaatt gcctaaggag ccataccata aattaaacca    960
tttgctgata tggccacaat ttttttaaca agctatgcca tagtcattca tgtgccacgg   1020 tgttgaatc gcctcaatta cgtgtggaac atgatggtgt tttaaacaac acttggtgat   1080
ttctattctg gcctactctt gcatctagga tcgtgttgtt agccatgtgc acatatttag   1140
ctagctagta gcaaaggcat gagtgagttg ctgatgggtt tacaaatacc agcataagta   1200
ttcattaatt tgaagtgaag cacgttcatg aacatatgag aaaacttaca ttataatttg   1260
cttggtcaga tgaaaccta gctgattcct tggcgacgac aacatccctc cttgttccat   1320
actttcttaa taattatttt tctcccaaaa agtccatcgc gctagcatca atgaagaaat   1380
ataagaaaaa tcctcatatc cacatagtaa atagagcatt atgcggtcca tgtaggaatc   1440
accttgggag cacctgcttg ctcaatcaca ctataaatac cacccataca ctgcttcaag   1500

<210> SEQ ID NO 6
<211> LENGTH: 104
<212> TYPE: DNA
<213> ORGANISM: Digitaria sanguinalis (L.) Scop.

<400> SEQUENCE: 6
agaaccatca cagacatacg ctacacgcac cctgtacgaa caaccaacct agctagctac     60
ctactgaaaa cacacataag cttgctaggc agcatatcat agca                     104

<210> SEQ ID NO 7
<211> LENGTH: 1407
<212> TYPE: DNA
<213> ORGANISM: Digitaria sanguinalis (L.) Scop.

<400> SEQUENCE: 7
atcttcaaga tgtcgtaatc gatttcttga gtcaaatatt ttgttttcat attatttagg     60 gagttttca tatggacaat acataaaaat atatatgcag tgcaagttat ttttgtttac    120
ttattcaatt tatccgttca atcccctaaa caaaatttta ccctaaacta ttttatttgg    180
tccaatctac accctaatta tatttctctt tttatttctc tgtgtctgag ttaaattttg    240
acttcaaatt ttatgaatag atgcaaaaca tgatgcttta tgctaaaaat ttttactaag    300 aaatttctt tgttatgttc ataggtcaag aatatttaat atgaaattga tcttacatat    360
ataaaactgt acaaaaagta atcatgaaaa aaattaatat atttgttcta acatagagca    420
ttatgtataa gtcaactgac aaaatttgaa attaaaactc agcttgcatg tgaagaaaca    480 aaaaagaga atctaatta gggtagatt ggaccaaata aaatagttta aggggggta    540 aaatgagcca aattttgttc aagggggttaa gtggatcaag taaatagatg aggggggtaa    600
```

```
aatggacttt tttcaacaat taacctcatc tatagaaggg taggtgcatc tcagttcgaa    660
aaataagatg catttggatc ttgaaaaatc aatttcccct cacaccccca aatggaaatt    720
gtcgtcacta ctcagataac taatgaaagt agactcttat tgtgatgatc caaaaggtct    780
ctgtgattgg aatttcgtcc acactatttt cacaacatcg taatgagata taatattgtt    840
ccaccagaaa gcctacctgc atggtcattt ctaataacca actcaaaaaa tggtaaatga    900
catgctcttt tagtgaaaaa ctttaaggaa cctagcttgc caaaatttat ctttgtcatt    960
aacaactcag tttcaaccat ccagtctcaa acaacttcac ttttttttt gcgggtaaaa   1020 caacttcact ttacatgtgg ccaaattgaa cacaacagtc acgtcccatt gaggtaccta   1080
gcaacttggg catcctttgt ctcgtacctc tacatatttt tgtccctgat caacacaaca   1140
ttcttaaacc catttccttg gcatttgccc atgttacaag gcgcaaaaca accaacccat   1200
atggcaattt actaaactaa actatgctga tccaatgcag caatcttgat cgctagtact   1260
gtccagcatt acatctgaaa caagtccaga tcacccatct catcacagtc acatgcatcc   1320
atggtcacgg gaaccgttaa cacacaccac caactaatcg gcattgctcc aatcctccta   1380
taaatacagc aacgatcagg cgagaca                                       1407

<210> SEQ ID NO 8
<211> LENGTH: 90
<212> TYPE: DNA
<213> ORGANISM: Digitaria sanguinalis (L.) Scop.

<400> SEQUENCE: 8
atacccaatc acacacagtg ttagcactta gcaaccgagg tatttctgcg agctttgtgc     60
ccttcttgtg gtcgagtaat tagtagcaaa                                      90

<210> SEQ ID NO 9
<211> LENGTH: 583
<212> TYPE: DNA
<213> ORGANISM: Miscanthus sinensis f. gracillimus

<400> SEQUENCE: 9
tctgctagat gcaacgagct ggaagccagg cctgggacaa ctcgttgatg ggcgtggggt     60
tcatcaaaca gagattagct tatcccattt tatgtagatg tgccatgtat gcatatgttt    120
tggaataatg gtgactcgtg aggaagcccg tgcacatgtt ttggaatgat ttctgccacc    180
gatcgcagaa ttcaaaataa ggcgagcaca tcagtgtttc gttaaaataa taaacggtag    240
attgaaataa tgattccagc tagcactata tattgtattt ctacgttaat aattttatat    300
attgcataag ggtcctccta attcatgcat cactagtagc tagcacgttg agtgtatttg    360
gcatggtttc tcaacttgct tcccctgtat cctgatcgat ctctccttca taactggcac    420
atcccaggac aaccaggcaa cgctcaaatc acacatgcgt tgctgattat ccacgctgca    480
tgatgcacga agccaatcac taaagcatca ccttccacac catcgttcag ctataaaaac    540
cctgccaaac tgcgtgagag gaccatccca aagcacaaga gca                      583

<210> SEQ ID NO 10
<211> LENGTH: 61
<212> TYPE: DNA
<213> ORGANISM: Miscanthus sinensis f. gracillimus

<400> SEQUENCE: 10
cgaagtgcag cactaaagca ccacttcctg ctcacaccgt tgtagtaata atccatcacc     60
``` a                                                              61

<210> SEQ ID NO 11
<211> LENGTH: 1500
<212> TYPE: DNA
<213> ORGANISM: Miscanthus sinensis f. gracillimus

<400> SEQUENCE: 11

| | | |
|---|---|---|
| ttgtgagaca aaaacactgt tgcggctggg aataagccgg ctgataagtt caagcgaaca | 60 |
| ggctgtactt tagtgcttct atttgaacca ttggttctca ctctggctat gcattgttgc | 120 |
| attctcactc tggcttataa ttttttcttg cctagtaata gttttgaaa taatgggagc | 180 |
| aaccacttca gttataatat aatgtttgta tgttataatg ggagcaatca ctctggttaa | 240 |
| ttgttgcctg tttataccat gcaggctgca ttatattaat tgcttagttc cttcttgttt | 300 |
| gtatgtgact atgagatttt tgtgacctct acaggaagtg aagggaagag gattcctgct | 360 |
| ggtttcaaca gacatagcaa gcaaagggtt tgcttctctg attgtgtatc tagatcacag | 420 |
| tagtgtgaat gtgcaccaag caaaacttaa attaggtgct ctatccatgt acattaagcc | 480 |
| tagctgtatc aaaaaaaatt cggtgttatc tgcgtaatat tggatgtata tataagattc | 540 |
| tggcattgga atttatattt tttttttgtt tttaattcat tatcacagac gcgtgttggt | 600 |
| cgtgcgcgtc tgtcataagg tgtcgtcaca gacgcgtttt gactatacgc gtctgtgata | 660 |
| gggttactac agacgcgtct ttactccacc agtctgtctt ataacctaat cgcagacgcg | 720 |
| tgtttgcata acgcagacgc ttattggtaa cacgcgtctg tagaagaaac ttattacaga | 780 |
| cacgttatta agcgcgtctg tgatgtgtct taacacgcgt ctgtaatgtg gatttattac | 840 |
| atagtgatcg gcccatatga acgaatgatc gatctaggcc caaagttagt gtatgaaatg | 900 |
| ttcatttacg tttcaatgcg gtttctcaaa aaaaaacgtt ccaatgctaa acaaaaacat | 960 |
| aggaattata tagttttgct gtggcttagt aacttcgtcc aatcgtgcta gtttaatttg | 1020 |
| tatatacctg taccatgcta ttcctctggc cttggttctt gcgcatccat tattaatgac | 1080 |
| cacgccacgc cacgcattca ttcttaatca ccagttgctt gacatccaat gtcctctcca | 1140 |
| ctacttgcgc acaccgtctg atactccaag atcccaagct aagataacac ccagtgatca | 1200 |
| tatatataaa aacaaacgcc agtgcgagcc tggccatttg cggagccaac cgaagccgtg | 1260 |
| cacaaaatat tcgataccgt atcagggaaa acactagtta tacgaggtag gcaataatcc | 1320 |
| atgtttcaaa aaaaacaggt aggcaataat ccagatcgga ctcttcctaa ccgggttcac | 1380 |
| atgcatatat gaatatgatg gccgggttca catgaacgct agatatcgtg cctagtagtg | 1440 |
| caccgatttc ttaatcccga ggctggacta taagtacccc tggtaacacc gtgatcaaag | 1500 |

<210> SEQ ID NO 12
<211> LENGTH: 98
<212> TYPE: DNA
<213> ORGANISM: Miscanthus sinensis f. gracillimus

<400> SEQUENCE: 12

| | | |
|---|---|---|
| catcgcaaac aagctgctaa tcacttctca agagctctct aactacatta attagctaga | 60 |
| gtgatccgcg aggtagctgg cttgtgatcg agcaatac | 98 |

<210> SEQ ID NO 13
<211> LENGTH: 740
<212> TYPE: DNA
<213> ORGANISM: Tripsacum dactyloides

<400> SEQUENCE: 13

```
aaatggatga acaaacttgg accaatcaga gatggccacg tcagctcccg atcgtcgtaa      60
ccgaccaaac ccgatcgata acggtttagg ctccaataca ccgtcggtac cacccggtcg     120
ctatcatctg cccccgtccc aacgctattg gtatcgtccg cccctatatc ggtcggtagc     180
ccagtccacc gtcggggcca atcgtcccct gctgcgtccg ctcgtgtcgg taccgatcgc     240
caaaaacgcc acgtcaacgg cactgcggta ccgaccgccg ctggcaccgg ccttagcggg     300
ccacacgacc gatcgctgtt gtacggacgt agaggtgaat catgcgattg aattttcgct     360
agaggaaagt tatcatctta ttatctccaa ccctccttcc tacggctgga tccgacgaaa     420
atttaccctg gacggtgcca gtaacaattg caggtctcac tcacgtgcta aatccagcaa     480
tcaaacacga aggaatatac gtgatctggc cagaacatgc aagagaataa tacagtagtg     540
ttagagtacg aaacctacac gattcaacga attaatcaat gggttcacgt tcacgggtat     600
gctcgcgcac gtccaaaatc aacgacatt tttataagcg gcatgatcca gacgggccag      660
ctcgagcacc acatggcgtg gctccatctc gcatccccca tcaccgctat aaataccatt     720
ggccatgcac acccgcactc                                                 740

<210> SEQ ID NO 14
<211> LENGTH: 91
<212> TYPE: DNA
<213> ORGANISM: Tripsacum dactyloides

<400> SEQUENCE: 14
ccacacagca caagcagcag cagcagcagc agctcgatcg aactagctta gctactacgt      60
gcgcgtgcaa caagcagctc gatcgatcgc c                                     91

<210> SEQ ID NO 15
<211> LENGTH: 903
<212> TYPE: DNA
<213> ORGANISM: Tripsacum dactyloides

<400> SEQUENCE: 15
actataattt tcatagagac catttctccc tccataccat ttaaaaaatt caaacaaaaa      60
atatctataa gtggccctag gttaagaaaa gtgccagtgg aaatgcatct ttattgacgg     120
ttttcttgta tctattgcca gtaaaaatca tatatttaca ttggcgattc tttgaagcat     180
accgtcatga caaatctgat ttctattgac agaatgctta agagaatcgc tattggtcat     240
ttagttgcag catttaattg gtatgttagt ctatgaaata gggaagtgga attttgtatt     300
gagagatatt gtttcattct tagttttacg acacctttga tgatgtagca gcgctggaaa     360
gagtgttatg aaattcctat tgagaatagc cttacaggtc aacagcatac ttttaaaatt     420
aaaccagaga tataccaaac ttcagtttct acgatataat attttttctac ctcataagtt     480 ataatcagtg gtacctcctt tttttttatat ccctttatta aggacggtag agaacgtcct     540
ctactcgtat gttgtacacc accgtaacg caattaagta aaacatgcat gtcaagtagt      600
aagtatataa gttggcaact caccagatgg caggagtcct gacccatcac cggctagcta     660
tagctcttgt tacgtgaatt cagcatgatt gctcaacttg cttctgtatt tccacatggg     720
ggagaattgt catatctccc cctaacaact ggcgcgtcca gagacaacca tgcaatgacc     780
aaaccgatcg aatcacacat gctttgcagc attcatgtac caatgctgcc aagcacgaaa     840 gcatctcccct ctccgctcca tccatcgtca gctataaaaa ccatgccaag cacctgtga      900 aaa                                                                   903
```

<210> SEQ ID NO 16
<211> LENGTH: 69
<212> TYPE: DNA
<213> ORGANISM: Tripsacum dactyloides

<400> SEQUENCE: 16

| | | | | | |
|---|---|---|---|---|---|
| gcatcccaaa | gcacacaaga | gcacgcagtg | cagcactcaa | gcacttcctg | ctcactgcac    60 |
| accgtacca | | | | |    69 |

<210> SEQ ID NO 17
<211> LENGTH: 1500
<212> TYPE: DNA
<213> ORGANISM: Tripsacum dactyloides

<400> SEQUENCE: 17

| | | | | | |
|---|---|---|---|---|---|
| aaaaggcact | tttctcaaga | acagagtta | gagatcaaac | caaagtgcta | gaaacattgt    60 |
| aataggtatg | tgcaacatat | ttaaaggttc | aaacctcaca | gttttaccct | ttttcacaaa   120 |
| gttgcacttc | ctggcctcgt | ttaagcttat | ttggacttag | aatcttcaaa | ttgtgctcga   180 |
| ttgaacctt | actcatatac | ttagcaaaca | agttagtcca | agatgttgtg | ttggacattc   240 |
| aatcaccaaa | acttatggaa | atggcttaat | tgcccatttc | cctttcatgg | tacaatttgt   300 |
| ttcacagatt | taagcagaag | ctatatcaaa | cacggcgctt | ctacaacagc | ttatcagttt   360 |
| agttgcttct | cagaatgaaa | ggtaataaac | ataagctgct | ttttactaga | tccttagata   420 |
| agttgctttt | ttaacaagca | gctctgccaa | gcagggccat | agtgccatgt | tgtaggctgg   480 |
| tcgctttccc | gagccatatg | aaggtcgtcg | gtccatgtgg | ctgaaattaa | agttgatagg   540 |
| cccatcggaa | caaatggtca | attagaggcc | caaaatttgt | gagtcaaatt | ttcatttaca   600 |
| cttccacgct | agtaaacgaa | aacatatata | gtacctatat | atcgattttt | tttttctggt   660 |
| gtcttagaaa | cttcgtccaa | taatcatgct | agtttaattt | gtatacctgc | acaaagctat   720 |
| tcctctggcc | ttggttcttt | gcgcgtccat | gcttgtttat | ggatgattgc | agccacgcca   780 |
| cgcattcatt | ctcaatcacc | atttgcttga | catctaatgt | cctctgcacc | acttgcgcac   840 |
| gctacacacc | gtctgatacg | ccaggatccc | aagctaaaat | aacacccaat | gatcatgtga   900 |
| aaacaagtga | cagtgcgagc | cagcccatgc | agcgatcttg | gccatttgcg | gagccaaccg   960 |
| aagccgtgca | caaatattc | gataccgtat | aaggggaaac | actagttata | cgaggtaggc  1020 |
| aaatataatc | ctcttcctaa | ccggcggccg | ggttcacatg | catatatgat | ggccgccagc  1080 |
| cgggttcaca | tgatgaacgc | tatggtgcct | agtgcacgat | ttattaatct | cccgaggctg  1140 |
| tactataaat | acatcggtaa | tactgtgatc | aaagcatcgc | aaagaagatc | tctaagactg  1200 |
| tctccagcaa | cgtcctctat | atctatcctc | tatatctgtc | ctttacagtc | tcctctaaaa  1260 |
| gattccatcc | tctatatctc | cttcctctcc | aacaacggcc | tctaaatcac | gtcctctata  1320 |
| cgcaaatacc | tatattagag | acatttttaa | ttttttaatt | tttgtacata | cgtatttgtc  1380 |
| atactctcaa | atgtattgta | catattttag | ttttgctaaa | ccggttgttt | aaagtattca  1440 |
| aatggataga | ggagaggaga | gagaaactct | atatatagag | gatccagcag | cgtcctctaa  1500 |

<210> SEQ ID NO 18
<211> LENGTH: 172
<212> TYPE: DNA
<213> ORGANISM: Tripsacum dactyloides

<400> SEQUENCE: 18

| | | | | | |
|---|---|---|---|---|---|
| atttagagga | ccgtttagag | gacgctgctg | gagggagtag | aggacgacag | cgttctctaa    60 |

```
aatttagagt acaggatact ttagaggacc tgctggaggc agtctaacaa ctgcatttgg    120
ctagagagag tgatcgcgag gtagctagct ggcttgtgat cgatcgagca aa            172
```

<210> SEQ ID NO 19
<211> LENGTH: 645
<212> TYPE: DNA
<213> ORGANISM: Saccharum officinarum

<400> SEQUENCE: 19

```
caaattaaag ttgataggcc catcggaaga aatgatcaat gtaaggccca aaatttgtgt     60
ctgaaatgtt cgtttacatt ttcaagctaa ataaaaacat aggaattata tagttttgct    120
ggtggcttag aaacttcgtc caaaatatta aaaaaaaga aaagaaactt cgtccaaaat     180
ggtgcttagt ttaatttgta tacctgcacc atgctattcc tctggccttg ttcttttgcg    240
catctatcca tgcctatgga tgatcgcagc cacgccacgc aattcattct taatcaccat    300
ttgcttgaca tccaatgtcc tctacaccac cacttgcgca ccctacacac cggccatttg    360
atacgccaag atcccaagct gaaataacac ccaatgatca tatgaaaaca agcgtgagtg    420
cgagcctgcc catgcagcga tcttggccat ttgcggagcc aaccgaagcc cgtgcacaaa    480
atattcgaga ccgtataagg gaaaacacta gttatacgca atgtccacaa taatccagat    540
cgactcttcc taaccgggtt cacatgaacg ctgttgtgcc tagtgcaccg atttcttaaa    600
tcccaaggct cgactataaa taccctggt atttgcaccg tgatc                     645
```

<210> SEQ ID NO 20
<211> LENGTH: 86
<212> TYPE: DNA
<213> ORGANISM: Saccharum officinarum

<400> SEQUENCE: 20

```
aaagcatcgc aaacaagcta aagagctctc taactacatt gattagagtg atctgcgcta     60
gaaggaggct agcttgtgat cgagca                                          86
```

<210> SEQ ID NO 21
<211> LENGTH: 1563
<212> TYPE: DNA
<213> ORGANISM: Setaria italica

<400> SEQUENCE: 21

```
agacccagca acctaccgag ggggtacccg aggtagtgtt ttgtggtggg gctcgtcgaa     60
gatcaggaac ttgaaggtga actcgaacac acgatttaga caagttcggg ctgcttatgc    120
cgcataatac cccatgtcat gtgtgttggt tggattgtat tgattgatca gatatttgga    180
gggggccctg cctcgcctta tattgcccat tgccggaggc agggctacag gtcggttgtt    240
gtacaagagt actagtcggt tttgaccagc gagtcctact ctaattgcta caagtagttt    300
cctaatcctt gactagtcct tgtccgccac gtagaccacg acgtcttgca cctagtctct    360
gtgtttgata catcttggtg tacagtccga tattgtagga ctatccaagc ttcccagtag    420
gcccatagat gtatggccga caactggata atgtaactct gggtcagtac tatccttatc    480
tatatagaca caaacaacgt actatagcag aagtttaagc tcgtaaccca ccaatatttg    540
gtggcataga ccacgtattg ctgatatagt gctcgtaacc caccaatatt tcgtggcata    600
gagatctctt aggcaataaa ttagcagtac gaaacaatct atgtccacgt gttgctaata    660
caatgttcta aaccttacag cctactggac agttctctag ccatgataca tgtgcatgtc    720
```

```
cgaacaaata tttatgggta cccgaaaggt taattttttg tagtatttat gagggggagg    780
ggggcgttga cgaaaaaaat aacttagcta agcgtaattg gcttaaaaac atacaatgtt    840
gttccagcat caagcctacg tgatcatttc acaaaaccaa ctcaaaagat aggtgtcatg    900
ttccttttag tgcaaaactt aaggacacct accttgcaaa acttagcttt gttacccaga    960
atgaaccgct aagctcgagg agctctgaac ttacatgacc aaatatatta aacacaaaag   1020
tcatgcatga ttttctttaa taagtatcga gcaatatggt tcgggtgtct ttcgtctcat   1080
acctctattg tcctccgtga tcaacaaggg tggatccggg tggtgcaagg gggctcaagc   1140
cccctacct ctcccaaagg agaagaagg gagaagaaag tgaaggaaga agaaaccccc      1200
tatattctaa tgctacctcc gccactgctg atcaacacaa cattcttaaa accatttcct   1260
tggcatttgc gcatgttaca aggtacaaaa gagccagccc atatgccaag ttactaaact   1320
aaactatgat ccaccatgga gcgagaacaa acgtcaacag gcatcaacca atgcagcaat   1380
cttgatcgct agtactgtcc ggcattatat ctgaaacaaa tccagatcac ccatctcatc   1440
acagtcacat gcattcatgg tcacgggaac cgttagcaaa ccaccaacta atcagcattg   1500
caacactctt cctcctataa atgcagcgag cgggggacac cataaaccat cacaggcact   1560
tag                                                                 1563

<210> SEQ ID NO 22
<211> LENGTH: 67
<212> TYPE: DNA
<213> ORGANISM: Setaria italica

<400> SEQUENCE: 22
cgatcaagtt aattttgttt ctgctttgtg cgcctgtgtt ccagtaatta ctttccgtgt     60
agcaaaa                                                               67

<210> SEQ ID NO 23
<211> LENGTH: 1528
<212> TYPE: DNA
<213> ORGANISM: Oryza sativa

<400> SEQUENCE: 23
ggaagctaac tagtcacggc gaatacatga cgacatcggc ctacaacgca caacttcttg     60
gcataaaagc ttcaatttca atgccccctat ctggaagccc taggcgccgc gcaaatgtaa   120
aacattcgct tcgcttggct tgttatccaa aatagagtat ggacctccga cagattggca   180
acccgtgggt aatcgaaaat ggctccatct gccccctttgt cgaaggaatc aggaaacggc   240
cctcacctcc tggcggagtg tagatatgtg aaagaatcta ggcgacactt gcagactgga   300
caacatgtga acaaataaga ccaacgttat ggcaacaagc ctcgacgcta ctcaagtggt   360
gggaggccac cgcatgttcc aacgaagcgc caaagaaagc cttgcagact ctaatgctat   420
tagtcgccta ggatatttgg aatgaaagga accgcagagt ttttcagcac caagagcttc   480
cggtggctag tctgatagcc aaaattaagg aggatgccaa acatgggtc ttggcgggcg    540
cgaaacacct tgataggtgg cttaccttt aacatgttcg ggccaaaggc cttgagacgg    600
taaagttttc tatttgcgct tgcgcatgta caatttatt cctctattca atgaaattgg     660
tggctcactg gttcattaaa aaaaaagaa tctagcctgt tcgggaagaa gaggattta      720
ttcgtgagag agagagagag agagagagag agagggagag agaaggagga ggaggatttt   780
caggcttcgc attgcccaac ctctgcttct gttggcccaa gaagaatccc aggcgcccat   840
gggctggcag tttaccacgg acctacctag cctaccttag ctatctaagc gggccgacct   900
```

```
agtagctacg tgcctagtgt agattaaagt tggcgggcca gcaggaagcc acgctgcaat    960
ggcatcttcc cctgtccttc gcgtacgtga aaacaaaccc aggtaagctt agaatcttct   1020
tgcccgttgg actgggacac ccaccaatcc caccatgccc cgatattcct ccggtctcgg   1080
ttcatgtgat gtcctctctt gtgtgatcac ggagcaagca ttcttaaacg caaaagaaa    1140 atcaccaact tgctcacgca gtcacgctgc accgcgcgaa gcgacgcccg ataggccaag   1200
atcgcgagat aaaataacaa ccaatgatca taaggaaaca agcccgcgat gtgtcgtgtg   1260
cagcaatctt ggtcatttgc gggatcgagt gcttcacggc taaccaaata ttcggccgat   1320
gatttaacac attatcagcg tagatgtacg tacgatttgt taattaatct acgagccttg   1380
ctagggcagg tgttctgcca gccaatccag atcgccctcg tatgcacgct cacatgatgg   1440
cagggcaggt ttcacatgag ctctaacggt cgattaatta atcccggggc tcgactataa   1500
atacctccct aatcccatga tcaaaacc                                     1528
```

<210> SEQ ID NO 24
<211> LENGTH: 99
<212> TYPE: DNA
<213> ORGANISM: Oryza sativa

<400> SEQUENCE: 24

```
atctcaagca gcctaatcat ctccagctga tcaagagctc ttaattagct agctagtgat    60
tagctgcgct tgtgatcgat cgatctcggg tacgtagca                           99
```

<210> SEQ ID NO 25
<211> LENGTH: 27
<212> TYPE: DNA
<213> ORGANISM: Artificial sequence
<220> FEATURE:
<221> NAME/KEY: misc_feature
<222> LOCATION: (1)..(27)
<223> OTHER INFORMATION: RCc3_Inter_1 amplification primer.

<400> SEQUENCE: 25

```
cagcacgttg gcgcacacgc ccagctt                                        27
```

<210> SEQ ID NO 26
<211> LENGTH: 27
<212> TYPE: DNA
<213> ORGANISM: Artificial sequence
<220> FEATURE:
<221> NAME/KEY: misc_feature
<222> LOCATION: (1)..(27)
<223> OTHER INFORMATION: RCc3_Outer_1 amplification primer.

<400> SEQUENCE: 26

```
gcacaccgcs gcctcsaggt cgacgag                                        27
```

<210> SEQ ID NO 27
<211> LENGTH: 27
<212> TYPE: DNA
<213> ORGANISM: Artificial sequence
<220> FEATURE:
<221> NAME/KEY: misc_feature
<222> LOCATION: (1)..(27)
<223> OTHER INFORMATION: RCc3_Inter_2 amplification primer.

<400> SEQUENCE: 27

```
aggttgatgc cgagsatgtt gsccttg                                        27
```

<210> SEQ ID NO 28

```
<211> LENGTH: 28
<212> TYPE: DNA
<213> ORGANISM: Artificial sequence
<220> FEATURE:
<221> NAME/KEY: misc_feature
<222> LOCATION: (1)..(28)
<223> OTHER INFORMATION: RCc3_Outer_2 amplification primer.

<400> SEQUENCE: 28
cttgccgcag trgttgagga kgaggctg                                    28

<210> SEQ ID NO 29
<211> LENGTH: 2001
<212> TYPE: DNA
<213> ORGANISM: Artificial sequence
<220> FEATURE:
<221> NAME/KEY: misc_feature
<222> LOCATION: (1)..(2001)
<223> OTHER INFORMATION: Codon redesigned GUS coding sequence with
      processable intron.

<400> SEQUENCE: 29
atggtgaggc cgttgagac cccgactagg gagatcaaga agctggacgg cctctgggcc      60
ttctccctcg accgtgagaa ctgcggcatc gaccagcgct ggtgggagtc cgccctccag    120
gagtctaggg ccatcgccgt gcccggtttc ttcaacgacc agttcgccga cgccgacatc    180
cgcaactacg cgggcaacgt ctggtatcag cgcgaggtgt tcatcccgaa gggctgggcg    240
ggccagcgca tcgtgctccg cttcgacgcc gtgacccact acggcaaggt ctgggtgaac    300
aatcaggagg taagtttctg cttctacctt tgatatatat ataataatta tcattaatta    360
gtagtaatat aatatttcaa atatttttt caaaataaaa gaatgtagta tatagcaatt    420
gcttttctgt agtttataag tgtgtatatt ttaatttata acttttctaa tatatgacca    480
aaatttgttg atgtgcaggt gatggagcac cagggcggtt acaccccgtt cgaggccgac    540
gtgacgccgt acgtgatcgc cgggaagtcc gtccgcatca ccgtctgcgt gaacaatgag    600
ctgaactggc agaccatccc gcctggcatg gtcatcaccg acgagaacgg caagaagaag    660
cagtcctact ccacgacttc ttcaactac gctggcatcc accgctccgt gatgctctac    720
accactccca cacctgggt ggacgacatc accgtggtca cccacgtggc ccaggactgc    780
aaccacgcct ccgtggactg gcaagtcgtt gccaacggcg acgtcagcgt cgagctgcgc    840
gacgccgacc agcaagtcgt tgccaccggc cagggcacca cggcaccct ccaagtcgtc    900 aaccctcacc tctggcagcc tggcgagggc tacctctacg agctgtgcgt caccgccaag    960
agccagactg agtgcgacat ctaccctctc cgcgtcggca tcaggagcgt cgctgtcaag   1020
ggcgagcagt tcctcatcaa ccacaagcct ttctacttca ctggtttcgg ccgccacgag   1080
gacgctgacc tgagggcaa gggtttcgac aacgtcctga tggtccacga ccacgctctg   1140
atggactgga tcggtgccaa cagctacagg accagtcact acccgtacgc tgaggagatg   1200
ctggactggg ctgacgagca cggtatcgtc gtgatcgacg agactgctgc ggtcggtttc   1260
aacctgtctc tgggcattgg tttcgaggct gggaacaagc cgaaggagct gtactctgag   1320
gaagctgtca acggcgagac tcagcaagct catctccagg cgattaagga gctgattgcc   1380
agggacaaga accatccgtc tgtcgtgatg tggtctattg cgaatgagcc ggacaccaga   1440
ccgcaagggg cgcgtgaata cttcgcgccg ctggcggagg cgactcgcaa actggaccca   1500
acccgtccaa tcacgtgcgt caatgtcatg ttctgcgacg cccatacgga tacgatctcg   1560
gacctgttcg atgttctttg tctcaatcgg tactatgggt ggtatgttca gagcgggat   1620
```

| | |
|---|---:|
| cttgagacgg cggagaaggt tcttgagaag gaactcctgg cgtggcaaga gaagctccat | 1680 |
| cagccgatca ttatcacgga gtacggggtt gacacacttg cgggccttca cagtatgtac | 1740 |
| acagatatgt ggtcggagga ataccagtgt gcatggttgg atatgtacca tcgtgtcttc | 1800 |
| gaccgggttt cagcggttgt cggcgaacaa gtctggaact cgcagactt cgccacgagc | 1860 |
| caagggatac tgcgggtagg agggaacaag aagggaatct tcacacggga tcggaagccc | 1920 |
| aagtcagcag ccttcctgtt gcagaagcga tggacaggaa tgaacttcgg agaaaagcca | 1980 |
| cagcaaggcg gaaagcagtg a | 2001 |

```
<210> SEQ ID NO 30
<211> LENGTH: 1812
<212> TYPE: DNA
<213> ORGANISM: Artificial sequence
<220> FEATURE:
<221> NAME/KEY: misc_feature
<222> LOCATION: (1)..(1812)
<223> OTHER INFORMATION: Codong redesigned GUS coding sequence.

<400> SEQUENCE: 30
```

| | |
|---|---:|
| atggtgaggc ccgttgagac cccgactagg gagatcaaga agctggacgg cctctgggcc | 60 |
| ttctccctcg accgtgagaa ctgcggcatc gaccagcgct ggtgggagtc cgccctccag | 120 |
| gagtctaggg ccatcgccgt gcccggttcc ttcaacgacc agttcgccga cgccgacatc | 180 |
| cgcaactacg cgggcaacgt ctggtatcag cgcgaggtgt tcatcccgaa gggctgggcg | 240 |
| ggccagcgca tcgtgctccg cttcgacgcc gtgacccact acggcaaggt ctgggtgaac | 300 |
| aatcaggagg tgatggagca ccagggcggt tacacccccgt tcgaggccga cgtgacgccg | 360 |
| tacgtgatcg ccgggaagtc cgtccgcatc accgtctgcg tgaacaatga gctgaactgg | 420 |
| cagaccatcc cgcctggcat ggtcatcacc gacgagaacg gcaagaagaa gcagtcctac | 480 |
| ttccacgact tcttcaacta cgctggcatc caccgctccg tgatgctcta caccactccc | 540 |
| aacacctggg tggacgacat caccgtggtc acccacgtgg cccaggactg caaccacgcc | 600 |
| tccgtggact ggcaagtcgt tgccaacggc gacgtcagcg tcgagctgcg cgacgccgac | 660 |
| cagcaagtcg ttgccaccgg ccagggcacc agcggcaccc tccaagtcgt caaccctcac | 720 |
| ctctggcagc tggcgagggc tacctctac gagctgtgcg tcaccgccaa gagccagact | 780 |
| gagtgcgaca tctaccctct ccgcgtcggc atcaggagcg tcgctgtcaa gggcgagcag | 840 |
| ttcctcatca accacaagcc tttctacttc actggtttcg gccgccacga ggacgctgac | 900 |
| ctgaggggca agggtttcga caacgtcctg atggtccacg accacgctct gatggactgg | 960 |
| atcggtgcca acagctacag gaccagtcac tacccgtacg ctgaggagat gctggactgg | 1020 |
| gctgacgagc acggtatcgt cgtgatcgac gagactgctg cggtcggttt caacctgtct | 1080 |
| ctgggcattg gtttcgaggc tgggaacaag ccgaaggagc tgtactctga ggaagctgtc | 1140 |
| aacggcgaga ctcagcaagc tcatctccag gcgattaagg agctgattgc cagggacaag | 1200 |
| aaccatccgt ctgtcgtgat gtggtctatt gcgaatgagc cggacaccag accgcaaggg | 1260 |
| gcgcgtgaat acttcgcgcc gctggcggag gcgactcgca aactggaccc aacccgtcca | 1320 |
| atcacgtgcg tcaatgtcat gttctgcgac gcccatacgg atacgatctc ggacctgttc | 1380 |
| gatgttcttt gtctcaatcg gtactatggg tggtatgttc agagcgggga tcttgagacg | 1440 |
| gcggagaagg ttcttgagaa ggaactcctg gcgtggcaag agaagctcca tcagccgatc | 1500 |
| attatcacga gtacgggggt tgacacactt gcgggccttc acagtatgta cacagatatg | 1560 |
| tggtcggagg aataccagtg tgcatggttg gatatgtacc atcgtgtctt cgaccgggtt | 1620 |

```
tcagcggttg tcggcgaaca agtctggaac ttcgcagact tcgccacgag ccaagggata    1680
ctgcgggtag gagggaacaa gaagggaatc ttcacacggg atcggaagcc caagtcagca    1740
gccttcctgt tgcagaagcg atggacagga atgaacttcg gagaaaagcc acagcaaggc    1800
ggaaagcagt ga                                                        1812

<210> SEQ ID NO 31
<211> LENGTH: 1812
<212> TYPE: DNA
<213> ORGANISM: Escherichia coli

<400> SEQUENCE: 31
atggtccgtc ctgtagaaac cccaacccgt gaaatcaaaa aactcgacgg cctgtgggca      60
ttcagtctgg atcgcgaaaa ctgtggaatt gatcagcgtt ggtgggaaag cgcgttacaa     120
gaaagccggg caattgctgt gccaggcagt tttaacgatc agttcgccga tgcagatatt     180
cgtaattatg cgggcaacgt ctggtatcag cgcgaagtct ttataccgaa aggttgggca     240
ggccagcgta tcgtgctgcg tttcgatgcg gtcactcatt acggcaaagt gtgggtcaat     300
aatcaggaag tgatggagca tcagggcggc tatacgccat ttgaagccga tgtcacgccg     360
tatgttattg ccgggaaaag tgtacgtatc accgtttgtg tgaacaacga actgaactgg     420
cagactatcc cgccgggaat ggtgattacc gacgaaaacg gcaagaaaaa gcagtcttac     480
ttccatgatt tctttaacta tgccggaatc catcgcagcg taatgctcta caccacgccg     540
aacacctggg tggacgatat caccgtggtg acgcatgtcg cgcaagactg taaccacgcg     600
tctgttgact ggcaggtggt ggccaatggt gatgtcagcg ttgaactgcg tgatgcggat     660
caacaggtgg ttgcaactgg acaaggcact agcgggactt gcaagtggt gaatccgcac     720 ctctggcaac cgggtgaagg ttatctctat gaactgtgcg tcacagccaa aagccagaca     780
gagtgtgata tctacccgct tcgcgtcggc atccggtcag tggcagtgaa gggcgaacag     840
ttcctgatta ccacaaaacc gttctacttt actggctttg gtcgtcatga agatgcggac     900
ttgcgtggca aaggattcga taacgtgctg atggtgcacg accacgcatt aatggactgg     960
attggggcca actcctaccg tacctcgcat taccttacg ctgaagagat gctcgactgg    1020
gcagatgaac atggcatcgt ggtgattgat gaaactgctg ctgtcggctt taacctctct    1080
ttaggcattg gtttcgaagc gggcaacaag ccgaaagaac tgtacagcga gaggcagtc    1140 aacggggaaa ctcagcaagc gcacttacag gcgattaaag agctgatagc gcgtgacaaa    1200
aaccacccaa gcgtggtgat gtggagtatt gccaacgaac cggataccg tccgcaaggt    1260 gcacgggaat atttcgcgcc actggcggaa gcaacgcgta aactcgaccc gacgcgtccg    1320
atcacctgcg tcaatgtaat gttctgcgac gctcacaccg ataccatcag cgatctcttt    1380
gatgtgctgt gcctgaaccg ttattacgga tggtatgtcc aaagcggcga tttggaaacg    1440
gcagagaagg tactgaaaaa agaacttctg cctggcagg agaaactgca tcagccgatt    1500
atcatcaccg aatacggcgt ggatacgtta gccgggctgc actcaatgta caccgacatg    1560
tggagtgaag agtatcagtg tgcatggctg gatatgtatc accgcgtctt tgatcgcgtc    1620
agcgccgtcg tcggtgaaca ggtatggaat ttcgccgatt ttgcgacctc gcaaggcata    1680
ttgcgcgttg gcggtaacaa gaagggatc ttcactcgcg accgcaaacc gaagtcggcg    1740
gcttttctgc tgcaaaaacg ctggactggc atgaacttcg gtgaaaaacc gcagcaggga    1800
ggcaaacaat ga                                                        1812
```

<210> SEQ ID NO 32
<211> LENGTH: 2001
<212> TYPE: DNA
<213> ORGANISM: Artificial sequence
<220> FEATURE:
<221> NAME/KEY: misc_feature
<222> LOCATION: (1)..(2001)
<223> OTHER INFORMATION: Chimeric coding sequence comprised of the
      native E. coli GUS coding sequence with a processable intron.

<400> SEQUENCE: 32

| | | | | | |
|---|---|---|---|---|---|
| atggtccgtc | ctgtagaaac | cccaacccgt | gaaatcaaaa | aactcgacgg | cctgtgggca | 60 |
| ttcagtctgg | atcgcgaaaa | ctgtggaatt | gatcagcgtt | ggtgggaaag | cgcgttacaa | 120 |
| gaaagccggg | caattgctgt | gccaggcagt | tttaacgatc | agttcgccga | tgcagatatt | 180 |
| cgtaattatg | cgggcaacgt | ctggtatcag | cgcgaagtct | ttataccgaa | aggttgggca | 240 |
| ggccagcgta | tcgtgctgcg | tttcgatgcg | gtcactcatt | acggcaaagt | gtgggtcaat | 300 |
| aatcaggaag | tgatggagca | tcagggcggc | tatacgccat | tgaagccga | tgtcacgccg | 360 |
| tatgttattg | ccgggaaaag | tgtacgtaag | tttctgcttc | tacctttgat | atatatataa | 420 |
| taattatcat | taattagtag | taatataata | tttcaaatat | ttttttcaaa | ataaaagaat | 480 |
| gtagtatata | gcaattgctt | ttctgtagtt | tataagtgtg | tatattttaa | tttataactt | 540 |
| ttctaatata | tgaccaaaat | ttgttgatgt | gcaggtatca | ccgtttgtgt | gaacaacgaa | 600 |
| ctgaactggc | agactatccc | gccgggaatg | gtgattaccg | acgaaaacgg | caagaaaaag | 660 |
| cagtcttact | tccatgattt | ctttaactat | gccggaatcc | atcgcagcgt | aatgctctac | 720 |
| accacgccga | cacctgggt | ggacgatatc | accgtggtga | cgcatgtcgc | gcaagactgt | 780 |
| aaccacgcgt | ctgttgactg | gcaggtggtg | gccaatggtg | atgtcagcgt | tgaactgcgt | 840 |
| gatgcggatc | aacaggtggt | tgcaactgga | caaggcacta | gcgggacttt | gcaagtggtg | 900 |
| aatccgcacc | tctggcaacc | gggtgaaggt | tatctctatg | aactgtgcgt | cacagccaaa | 960 |
| agccagacag | agtgtgatat | ctacccgctt | cgcgtcggca | tccggtcagt | ggcagtgaag | 1020 |
| ggcgaacagt | tcctgattaa | ccacaaaccg | ttctacttta | ctggctttgg | tcgtcatgaa | 1080 |
| gatgcggact | tgcgtggcaa | aggattcgat | aacgtgctga | tggtgcacga | ccacgcatta | 1140 |
| atggactgga | ttggggccaa | ctcctaccgt | acctcgcatt | acccttacgc | tgaagagatg | 1200 |
| ctcgactggg | cagatgaaca | tggcatcgtg | gtgattgatg | aaactgctgc | tgtcggcttt | 1260 |
| aacctctctt | taggcattgg | tttcgaagcg | ggcaacaagc | cgaaagaact | gtacagcgaa | 1320 |
| gaggcagtca | acgggaaac | tcagcaagcg | cacttacagg | cgattaaaga | gctgatagcg | 1380 |
| cgtgacaaaa | accacccaag | cgtggtgatg | tggagtattg | ccaacgaacc | ggatacccgt | 1440 |
| ccgcaaggtg | cacgggaata | tttcgcgcca | ctggcggaag | caacgcgtaa | actcgacccg | 1500 |
| acgcgtccga | tcacctgcgt | caatgtaatg | ttctgcgacg | ctcacaccga | taccatcagc | 1560 |
| gatctctttg | atgtgctgtg | cctgaaccgt | tattacggat | ggtatgtcca | aagcggcgat | 1620 |
| ttggaaacgg | cagagaaggt | actggaaaaa | gaacttctgg | cctggcagga | gaaactgcat | 1680 |
| cagccgatta | tcatcaccga | atacggcgtg | gatacgttag | ccgggctgca | ctcaatgtac | 1740 |
| accgacatgt | ggagtgaaga | gtatcagtgt | gcatggctgg | atatgtatca | ccgcgtcttt | 1800 |
| gatcgcgtca | gcgccgtcgt | cggtgaacag | gtatggaatt | tcgccgattt | tgcgacctcg | 1860 |
| caaggcatat | tgcgcgttgg | cggtaacaag | aaagggatct | cactcgcga | ccgcaaaccg | 1920 |
| aagtcggcgg | cttttctgct | gcaaaaacgc | tggactggca | tgaacttcgg | tgaaaaaccg | 1980 | cagcagggag gcaaacaatg a                                              2001

<210> SEQ ID NO 33
<211> LENGTH: 435
<212> TYPE: DNA
<213> ORGANISM: Setaria italica

<400> SEQUENCE: 33
ggcgcccttt gagaagaagc ttttggtctg ctgcgcttat catgttttgt ggcttctgtg      60
ttgtgattct tgatctgccc cttgctatca tttgtattgt actgtcctaa taagtggtac     120
ttgtgagggt attactgtgt ctggttattt acctagagga ggaattattg tctgctattt     180
ctggttttgc tgtttatgta atggtgaacc aaagaatgaa gctgcaggct actttgagaa     240
ggaaggggac ctgctgcttt ctatcttgtc atgcgtgatt acttgaacag tcctgatgat     300
ctattaatgt tctttggtca gtgcaagtgt ttggtgtagc ccaacaggt agtgtttatg      360
tttggtgaag cagcaatggc cgactgtatg tgtttggtga agctgcaacc tgcttgtgct     420
aactgaacat gcaga                                                     435

<210> SEQ ID NO 34
<211> LENGTH: 2219
<212> TYPE: DNA
<213> ORGANISM: Artificial sequence
<220> FEATURE:
<221> NAME/KEY: misc_feature
<222> LOCATION: (1)..(2219)
<223> OTHER INFORMATION: Chimeric transcriptional regulatory expression
      element group (EXP).

<400> SEQUENCE: 34
attatggcca attatttatc ggcctggtcc tggcaggatg agtgtagtag tgtacctaat      60
ttggtaggca atgggtttga gttaggccaa taaatgtgca ggtttacatt tggttgccat     120
gttagttcat aacttcatac acttccattt ttgtacgtcg gcgatgtttc aaccagaaca     180
gattatgttt ccttgggact gtaaatttct tcatcgctcc atcccaatga acttgcaaga     240
gattcgtgtt agcaaccaaa attgctctgt ccttcccaaa aagcattgcc tctggatctt     300
ttccgatcaa gatcagaaac cctatatgta ttgttcttat gttctgctgt gggtcgttgg     360
ttcttgtcac ccttaaactt ctctgtttgg tacccagata aatacaaatt cggctggtgg     420
gtagaaaaac cgcctacgaa cactggtttc accttataag actactgcac tgtttctagc     480
aggcttattt ttctcttcgt tttttatatt ccaatgtata catattaatg tttatcgagc     540
tatgatctta taaatttgta catgcttcaa tattttctaa aaacttgaat aacagtatgt     600
aaaacctagg ttgatgtttc aaatgaactt atttaacatt ttacgttgaa acagtacatc     660
gcgaatggca tattattttg ttgcatttat tctaaacacc ttaaaatgga atttgaaaac     720
gggctctaag tttgagagaa gtttaagggt aatagtattc taaacacttc aagtttgaga     780
tccaaaataa ttaatctctc acctatcacc tccaatcaag ttgttatca gtttatgcca      840
tgtacatgta tcgctggttt gttatttcac ctcattttcg ctatgtatct actactattg     900
cgctaatctc aaatattaga tgacatgtaa actaaaatct ttggaaagat taataggata     960
cccgcgggtg ctgatatctg tttctaaaaa tgttgaatct aactatttgt aaatattgat    1020
atatttttca gaaatgttgg atttagtctt gtgaaatgtt gaaccgatat ctctgatatg    1080
gatttaatgg gcttaaagct tccactagcc gtgtgcatgg gcgaaaaaaa atcttggcca    1140
agtgttactc cgtcgcggcc acacgccaca agtcctcccg gccctcgctc gccccttatc    1200

```
ccatcgtacc cgccacacgg cgcgccacca gtggcgccgc ggatgcgcct catctccccg    1260
gcggccacct cgcgcggttt agatttccct gggcccccct cgcggtaccg tcacatattt    1320
ttggcgcctc ttcttctgcg ccccctctcct cccgaaccgc agataccacc gagtcggcag   1380
ctgaacacaa gcaacaagca agtgatcccg gaccgaccgt cttcggtacg cgctcactcc    1440
gccctctgcc tttgttactg ccacgtttct ctgaatgctc tcttgtgtgg tgattgctga    1500
gagtggttta gctggatcta gaattacact ctgaaatcgt gttctgcctg tgctgattac    1560
ttgccgtcct ttgtagcagc aaaatatagg gacatggtag tacgaaacga agatagaacc    1620
tacacagcaa tacgagaaat gtgtaatttg gtgcttagcg gtatttattt aagcacatgt    1680
tggtgttata gggcacttgg attcagaagt ttgctgttaa tttaggcaca ggcttcatac    1740
tacatgggtc aatagtatag ggattcatat tataggcgat actataataa tttgttcgtc    1800
tgcagagctt attatttgcc aaaattagat attcctattc tgttttttgtt tgtgtgctgt   1860 taaattgtta acgcctgaag gaataaatat aaatgacgaa attttgatgt ttatctctgc    1920
tcctttattg tgaccataag tcaagatcag atgcacttgt tttaaatatt gttgtctgaa    1980
gaaataagta ctgacagtat tttgatgcat tgatctgctt gtttgttgta acaaaattta    2040
aaaataaaga gtttccttt tgttgctctc cttacctcct gatggtatct agtatctacc     2100
aactgacact atattgcttc tctttacata cgtatcttgc tcgatgcctt ctccctagtg    2160
ttgaccagtg ttactcacat agtctttgct catttcattg taatgcagat accaagcgg     2219
```

<210> SEQ ID NO 35
<211> LENGTH: 2224
<212> TYPE: DNA
<213> ORGANISM: Artificial sequence
<220> FEATURE:
<221> NAME/KEY: misc_feature
<222> LOCATION: (1)..(2224)
<223> OTHER INFORMATION: Chimeric transcriptional regulatory expression element group (EXP).

<400> SEQUENCE: 35

```
attatggcca attatttatc ggcctggtcc tggcaggatg agtgtagtag tgtacctaat      60
ttggtaggca atgggtttga gttaggccaa taaatgtgca ggtttacatt tggttgccat     120
gttagttcat aacttcatac acttccattt ttgtacgtcg gcgatgtttc aaccagaaca     180
gattatgttt ccttgggact gtaaatttct tcatcgctcc atcccaatga acttgcaaga     240
gattcgtgtt agcaaccaaa attgctctgt ccttcccaaa aagcattgcc tctggatctt     300
ttccgatcaa gatcagaaac cctatatgta ttgttcttat gttctgctgt gggtcgttgg     360
ttcttgtcac ccttaaactt ctctgtttgg tacccagata aatacaaatt cggctggtgg     420
gtagaaaaac cgcctacgaa cactggtttc accttataag actactgcac tgtttctagc     480
aggcttattt ttctcttcgt tttttatatt ccaatgtata catattaatg tttatcgagc     540
tatgatctta taaatttgta catgcttcaa tattttctaa aaacttgaat aacagtatgt     600
aaaacctagg ttgatgtttc aaatgaactt atttaacatt ttacgttgaa acagtacatc     660
gcgaatggca tattatttg ttgcatttat tctaaacacc ttaaaatgga atttgaaaac      720
gggctctaag tttgagagaa gtttaagggt aatagtattc taaacacttc aagtttgaga    780
tccaaaataa ttaatctctc acctatcacc tccaatcaag ttgtttatca gtttatgcca    840
tgtacatgta tcgctggttt gttatttcac ctcattttcg ctatgtatct actactattg    900
cgctaatctc aaatattaga tgacatgtaa actaaaatct ttggaaagat taataggata    960
```

```
cccgcgggtg ctgatatctg tttctaaaaa tgttgaatct aactatttgt aaatattgat    1020 atattttca gaaatgttgg atttagtctt gtgaaatgtt gaaccgatat ctctgatatg     1080
gatttaatgg gcttaaagct tccactagcc gtgtgcatgg gcgaaaaaaa atcttggcca    1140
agtgttactc cgtcgcggcc acacgccaca agtcctcccg gccctcgctc gccccttatc    1200
ccatcgtacc cgccacacgg cgcgccacca gtggcgccgc ggatgcgcct catctccccg    1260
gcggccacct cgcgcggttt agatttccct gggcccccct cgcggtaccg tcacatattt    1320
ttggcgcctc ttcttctgcg cccctctcct cccgaaccgc agataccacc gagtcggcag    1380
ctgaacacaa gcaacaagca agtgatcccg gaccggaccg accgtcttcg gtacgcgctc    1440
actccgccct ctgcctttgt tactgccacg tttctctgaa tgctctcttg tgtggtgatt    1500
gctgagagtg gtttagctgg atctagaatt acactctgaa atcgtgttct gcctgtgctg    1560
attacttgcc gtcctttgta gcagcaaaat atagggacat ggtagtacga aacgaagata    1620
gaacctacac agcaatacga gaaatgtgta atttggtgct tagcggtatt tatttaagca    1680
catgttggtg ttatagggca cttggattca gaagtttgct gttaatttag gcacaggctt    1740
catactacat gggtcaatag tatagggatt catattatag gcgatactat aataatttgt    1800
tcgtctgcag agcttattat ttgccaaaat tagatattcc tattctgttt ttgtttgtgt    1860
gctgttaaat tgttaacgcc tgaaggaata aatataaatg acgaaatttt gatgtttatc    1920
tctgctcctt tattgtgacc ataagtcaag atcagatgca cttgttttaa atattgttgt    1980
ctgaagaaat aagtactgac agtattttga tgcattgatc tgcttgtttg ttgtaacaaa    2040
atttaaaaat aaagagtttc cttttttgttg ctctccttac ctcctgatgg tatctagtat    2100
ctaccaactg acactatatt gcttctcttt acatacgtat cttgctcgat gccttctccc    2160
tagtgttgac cagtgttact cacatagtct ttgctcattt cattgtaatg cagataccaa    2220
gcgg                                                                  2224
```

<210> SEQ ID NO 36
<211> LENGTH: 2966
<212> TYPE: DNA
<213> ORGANISM: Artificial sequence
<220> FEATURE:
<221> NAME/KEY: misc_feature
<222> LOCATION: (1)..(2966)
<223> OTHER INFORMATION: Chimeric transcriptional regulatory expression
      element group (EXP).

<400> SEQUENCE: 36

```
ggtccgattg agacttttca acaaagggta atatccggaa acctcctcgg attccattgc     60
ccagctatct gtcactttat tgtgaagata gtggaaaagg aaggtggctc ctacaaatgc    120
catcattgcg ataaaggaaa ggccatcgtt gaagatgcct ctgccgacag tggtcccaaa    180
gatggacccc cacccacgag gagcatcgtg aaaaagaag acgttccaac cacgtcttca     240
aagcaagtgg attgatgtga tggtccgatt gagacttttc aacaaagggt aatatccgga    300
aacctcctcg gattccattg cccagctatc tgtcactttta ttgtgaagat agtggaaaag    360
gaaggtggct cctacaaatg ccatcattgc gataaaggaa aggccatcgt tgaagatgcc    420
tctgccgaca gtggtcccaa agatggaccc ccacccacga ggagcatcgt ggaaaagaa     480 gacgttccaa ccacgtcttc aaagcaagtg gattgatgtg atcggaagct aactagtcac    540
ggcgaataca tgacgacatc ggcctacaac gcacaacttc ttggcataaa agcttcaatt    600
tcaatgcccc tatctggaag ccctaggcgc cgcgcaaatg taaaacattc gcttcgcttg    660
```

```
gcttgttatc caaaatagag tatggacctc cgacagattg gcaacccgtg ggtaatcgaa      720
aatggctcca tctgcccctt tgtcgaagga atcaggaaac ggccctcacc tcctggcgga      780
gtgtagatat gtgaaagaat ctaggcgaca cttgcagact ggacaacatg tgaacaaata      840
agaccaacgt tatggcaaca agcctcgacg ctactcaagt ggtgggaggc caccgcatgt      900
tccaacgaag cgccaaagaa agccttgcag actctaatgc tattagtcgc ctaggatatt      960
tggaatgaaa ggaaccgcag agttttcag caccaagagc ttccggtggc tagtctgata     1020
gccaaaatta aggaggatgc caaaacatgg gtcttggcgg gcgcgaaaca ccttgatagg     1080
tggcttacct tttaacatgt tcgggccaaa ggccttgaga cggtaaagtt ttctatttgc     1140
gcttgcgcat gtacaatttt attcctctat tcaatgaaat tggtggctca ctggttcatt     1200
aaaaaaaaaa gaatctagcc tgttcgggaa gaagaggatt ttattcgtga gagagagaga     1260
gagagagaga gagagaggga gagagaagga ggaggaggat tttcaggctt cgcattgccc     1320
aacctctgct tctgttggcc caagaagaat cccaggcgcc catgggctgg cagtttacca     1380
cggacctacc tagcctacct tagctatcta agcgggccga cctagtagct acgtgcctag     1440
tgtagattaa agttggcggg ccagcaggaa gccacgctgc aatggcatct tcccctgtcc     1500
ttcgcgtacg tgaaaacaaa cccaggtaag cttagaatct tcttgcccgt tggactggga     1560
cacccaccaa tcccaccatg ccccgatatt cctccggtct cggttcatgt gatgtcctct     1620
cttgtgtgat cacggagcaa gcattcttaa acggcaaaag aaaatcacca acttgctcac     1680
gcagtcacgc tgcaccgcgc gaagcgacgc ccgataggcc aagatcgcga gataaaataa     1740
caaccaatga tcataaggaa acaagcccgc gatgtgtcgt gtgcagcaat cttggtcatt     1800
tgcgggatcg agtgcttcac ggctaaccaa atattcggcc gatgatttaa cacattatca     1860
gcgtagatgt acgtacgatt tgttaattaa tctacgagcc ttgctagggc aggtgttctg     1920
ccagccaatc cagatcgccc tcgtatgcac gctcacatga tggcagggca gggttcacat     1980
gagctctaac ggtcgattaa ttaatcccgg ggctcgacta taaataccct cctaatccca     2040
tgatcaaaac catctcaagc agcctaatca tctccagctg atcaagagct cttaattagc     2100
tagctagtga ttagctgcgc ttgtgatcga tcgatctcgg gtacgtagca cggaccggac     2160
cgaccgtctt cggtacgcgc tcactccgcc ctctgccttt gttactgcca cgtttctctg     2220
aatgctctct tgtgtggtga ttgctgagag tggtttagct ggatctagaa ttacactctg     2280
aaatcgtgtt ctgcctgtgc tgattacttg ccgtcctttg tagcagcaaa atatagggac     2340
atggtagtac gaaacgaaga tagaacctac acagcaatac gagaaatgtg taatttggtg     2400
cttagcggta tttatttaag cacatgttgg tgttataggg cacttggatt cagaagtttg     2460 ctgttaatt aggcacaggc ttcatactac atgggtcaat agtatag ga ttcatattat     2520 aggcgatact ataataattt gttcgtctgc agagcttatt atttgccaaa attagatatt     2580
cctattctgt ttttgtttgt gtgctgttaa attgttaacg cctgaaggaa taaatataaa     2640
tgacgaaatt ttgatgttta tctctgctcc tttattgtga ccataagtca agatcagatg     2700
cacttgtttt aaatattgtt gtctgaagaa ataagtactg acagtatttt gatgcattga     2760
tctgcttgtt tgttgtaaca aaatttaaaa ataaagagtt tccttttgt tgctctcctt      2820 acctcctgat ggtatctagt atctaccaac tgacactata ttgcttctct ttacatacgt     2880
atcttgctcg atgccttctc cctagtgttg accagtgtta ctcacatagt ctttgctcat     2940
ttcattgtaa tgcagatacc aagcgg                                          2966
```

<210> SEQ ID NO 37
<211> LENGTH: 2005
<212> TYPE: DNA
<213> ORGANISM: Zea mays subsp. Mexicana

<400> SEQUENCE: 37

```
gtcgtgcccc tctctagaga taaagagcat tgcatgtcta aagtataaaa aattaccaca       60
tatttttttg tcacacttat ttgaagtgta gtttatctat ctctatacat atatttaaac      120
ttcactctac aaataatata gtctataata ctaaaataat attagtgttt tagaggatca      180
tataaataaa ctgctagaca tggtctaaag gataattgaa tattttgaca atctacagtt      240
ttatctttt agtgtgcatg tgatctctct gtttttttg caaatagctt gacctatata        300
atacttcatc cattttatta gtacatccat ttaggattta gggttgatgg tttctataga      360
ctaattttta gtacatccat tttattcttt ttagtctcta aatttttaa aactaaaact       420
ctattttagt tttttattta ataatttaga tataaaatga aataaaataa attgactaca      480
aataaaacaa atacccttta agaaataaaa aaactaagca aacattttc ttgtttcgag       540
tagataatga caggctgttc aacgccgtcg acgagtctaa cggacaccaa ccagcgaacc      600
agcagcgtcg cgtcgggcca agcgaagcag acggcacggc atctctgtag ctgcctctgg      660
acccctctcg agagttccgc tccaccgttg gacttgctcc gctgtcggca tccagaaatt      720
gcgtggcgga gcggcagacg tgaggcggca cggcaggcgg cctcttcctc ctctcacggc      780
accggcagct acgggggatt cctttcccac cgctccttcg ctttcccttc ctcgcccgcc      840
gtaataaata gacacccct ccacaccctc tttccccaac ctcgtgttcg ttcggagcgc       900
acacacacgc aaccagatct cccccaaatc cagccgtcgg cacctccgct tcaaggtacg      960
ccgctcatcc tcccccccc cctctctcta ccttctctag atcggcgatc cggtccatgg     1020
ttagggcccg gtagttctac ttctgttcat gtttgtgtta gagcaaacat gttcatgttc     1080
atgtttgtga tgatgtggtc tggttgggcg gtcgttctag atcggagtag gatactgttt     1140
caagctacct ggtggattta ttaattttgt atctgtatgt gtgtgccata catcttcata     1200
gttacgagtt taagatgatg gatggaaata tcgatctagg ataggtatac atgttgatgc     1260
gggttttact gatgcatata cagagatgct ttttttctcg cttggttgtg atgatatggt     1320
ctggttgggc ggtcgttcta gatcggagta gaatactgtt tcaaactacc tggtggattt     1380
attaaaggat aaagggtcgt tctagatcgg agtagaaac tgtttcaaac tacctggtgg      1440
atttattaaa ggatctgtat gtatgtgcct acatcttcat agttacgagt ttaagatgat     1500
ggatggaaat atcgatctag gataggtata catgttgatg cgggttttac tgatgcatat     1560
acagagatgc ttttttcgc ttggttgtga tgatgtggtc tggttgggcg gtcgttctag      1620
atcggagtag aatactgttt caaactacct ggtggattta ttaattttgt atctttatgt     1680
gtgtgccata catcttcata gttacgagtt taagatgatg gatggaaata ttgatctagg     1740
ataggtatac atgttgatgt gggttttact gatgcatata catgatggca tatgcggcat     1800
ctattcatat gctctaacct tgagtaccta tctattataa taaacaagta tgttttataa     1860
ttattttgat cttgatatac ttggatgatg gcatatgcag cagctatatg tggattttt      1920
agccctgcct tcatacgcta tttatttgct tggtactgtt tcttttgtcc gatgctcacc     1980
ctgttgttgg gtgatacttc tgcag                                          2005
```

<210> SEQ ID NO 38
<211> LENGTH: 804
<212> TYPE: DNA

<213> ORGANISM: Oryza sativa

<400> SEQUENCE: 38

```
accgtcttcg gtacgcgctc actccgccct ctgcctttgt tactgccacg tttctctgaa      60
tgctctcttg tgtggtgatt gctgagagtg gtttagctgg atctagaatt acactctgaa     120
atcgtgttct gcctgtgctg attacttgcc gtcctttgta gcagcaaaat atagggacat     180
ggtagtacga aacgaagata gaacctacac agcaatacga gaaatgtgta atttggtgct     240
tagcggtatt tatttaagca catgttggtg ttatagggca cttggattca gaagtttgct     300
gttaatttag gcacaggctt catactacat gggtcaatag tatagggatt catattatag     360
gcgatactat aataatttgt tcgtctgcag agcttattat ttgccaaaat tagatattcc     420
tattctgttt ttgtttgtgt gctgttaaat tgttaacgcc tgaaggaata aatataaatg     480
acgaaatttt gatgtttatc tctgctcctt tattgtgacc ataagtcaag atcagatgca     540
cttgttttaa atattgttgt ctgaagaaat aagtactgac agtattttga tgcattgatc     600
tgcttgtttg ttgtaacaaa atttaaaaat aaagagtttc cttttttgttg ctctccttac     660
ctcctgatgg tatctagtat ctaccaactg acactatatt gcttctcttt acatacgtat     720
cttgctcgat gccttctccc tagtgttgac cagtgttact cacatagtct ttgctcattt     780
cattgtaatg cagataccaa gcgg                                            804
```

<210> SEQ ID NO 39
<211> LENGTH: 253
<212> TYPE: DNA
<213> ORGANISM: Agrobacterium tumefaciens

<400> SEQUENCE: 39

```
gatcgttcaa acatttggca ataaagtttc ttaagattga atcctgttgc cggtcttgcg      60
atgattatca tataatttct gttgaattac gttaagcatg taataattaa catgtaatgc     120
atgacgttat ttatgagatg ggtttttatg attagagtcc cgcaattata catttaatac     180
gcgatagaaa acaaaatata gcgcgcaaac taggataaat tatcgcgcgc ggtgtcatct     240
atgttactag atc                                                        253
```

<210> SEQ ID NO 40
<211> LENGTH: 300
<212> TYPE: DNA
<213> ORGANISM: Oryza sativa

<400> SEQUENCE: 40

```
attaatcgat cctccgatcc cttaattacc ataccattac accatgcatc aatatccata      60
tatatataaa cccttcgca cgtacttata ctatgttttg tcatacatat atatgtgtcg     120
aacgatcgat ctatcactga tatgatatga ttgatccatc agcctgatct ctgtatcttg     180
ttatttgtat accgtcaaat aaaagtttct tccacttgtg ttaataatta gctactctca     240
tctcatgaac cctatatata actagtttaa tttgctgtca attgaacatg atgatcgatg     300
```

<210> SEQ ID NO 41
<211> LENGTH: 1446
<212> TYPE: DNA
<213> ORGANISM: Artificial sequence
<220> FEATURE:
<221> NAME/KEY: misc_feature
<222> LOCATION: (1)..(1446)
<223> OTHER INFORMATION: Chimeric transcriptional regulatory expression
      element group (EXP).

-continued

```
<400> SEQUENCE: 41
ggtccgattg agacttttca acaaagggta atatccggaa acctcctcgg attccattgc      60
ccagctatct gtcactttat tgtgaagata gtggaaaagg aaggtggctc ctacaaatgc     120
catcattgcg ataaaggaaa ggccatcgtt gaagatgcct ctgccgacag tggtcccaaa     180
gatggacccc cacccacgag gagcatcgtg gaaaagaag acgttccaac cacgtcttca      240
aagcaagtgg attgatgtga tggtccgatt gagacttttc aacaaagggt aatatccgga     300
aacctcctcg gattccattg cccagctatc tgtcactttat ttgtgaagat agtggaaaag    360
gaaggtggct cctacaaatg ccatcattgc gataaaggaa aggccatcgt tgaagatgcc     420
tctgccgaca gtggtcccaa agatggaccc ccacccacga ggagcatcgt ggaaaaagaa     480
gacgttccaa ccacgtcttc aaagcaagtg gattgatgtg atatctccac tgacgtaagg     540
gatgacgcac aatcccacta tccttcgcaa gaccttcct ctatataagg aagttcattt      600
catttggaga ggacacgctg acaagctgac tctagcagat ctaccgtctt cggtacgcgc     660
tcactccgcc ctctgccttt gttactgcca cgtttctctg aatgctctct tgtgtggtga     720
ttgctgagag tggtttagct ggatctagaa ttacactctg aaatcgtgtt ctgcctgtgc     780
tgattacttg ccgtcctttg tagcagcaaa atataggac atggtagtac gaaacgaaga      840
tagaacctac acagcaatac gagaaatgtg taatttggtg cttagcggta tttatttaag     900
cacatgttgg tgttataggg cacttggatt cagaagtttg ctgttaattt aggcacaggc     960
ttcatactac atgggtcaat agtataggga ttcatattat aggcgatact ataataattt    1020
gttcgtctgc agagcttatt atttgccaaa attagatatt cctattctgt ttttgtttgt    1080
gtgctgttaa attgttaacg cctgaaggaa taaatataaa tgacgaaatt ttgatgttta    1140
tctctgctcc tttattgtga ccataagtca agatcagatg cacttgtttt aaatattgtt    1200
gtctgaagaa ataagtactg acagtatttt gatgcattga tctgcttgtt tgttgtaaca    1260
aaatttaaaa ataagagtt tccttttgt tgctctcctt acctcctgat ggtatctagt      1320
atctaccaac tgacactata ttgcttctct ttacatacgt atcttgctcg atgccttctc    1380
cctagtgttg accagtgtta ctcacatagt ctttgctcat ttcattgtaa tgcagatacc    1440
aagcgg                                                               1446

<210> SEQ ID NO 42
<211> LENGTH: 1653
<212> TYPE: DNA
<213> ORGANISM: Photinus pyralis

<400> SEQUENCE: 42
atggaagacg ccaaaaacat aaagaaaggc ccggcgccat tctatcctct agaggatgga     60
accgctggag agcaactgca taaggctatg aagagatacg ccctggttcc tggaacaatt    120
gcttttacag atgcacatat cgaggtgaac atcacgtacg cggaatactt cgaaatgtcc    180
gttcggttgg cagaagctat gaaacgatat gggctgaata caaatcacag aatcgtcgta    240
tgcagtgaaa actctcttca attctttatg ccggtgttgg gcgcgttatt tatcggagtt    300
gcagttgcgc ccgcgaacga catttataat gaacgtgaat tgctcaacag tatgaacatt    360
tcgcagccta ccgtagtgtt tgtttccaaa aagggggttgc aaaaaatttt gaacgtgcaa    420
aaaaaattac caataatcca gaaaattatt atcatggatt ctaaaacgga ttaccaggga    480
tttcagtcga tgtacacgtt cgtcacatct catctacctc ccggttttaa tgaatacgat    540
tttgtaccag agtcctttga tcgtgacaaa acaattgcac tgataatgaa ttcctctgga    600
```

```
tctactgggt tacctaaggg tgtggcccct ccgcatagaa ctgcctgcgt cagattctcg    660
catgccagag atcctatttt tggcaatcaa atcattccgg atactgcgat tttaagtgtt    720
gttccattcc atcacggttt tggaatgttt actacactcg atatttgat atgtggattt     780 cgagtcgtct taatgtatag atttgaagaa gagctgtttt tacgatccct tcaggattac    840
aaaattcaaa gtgcgttgct agtaccaacc ctatttcat tcttcgccaa aagcactctg     900
attgacaaat acgattatc taatttacac gaaattgctt ctgggggcgc acctctttcg     960
aaagaagtcg gggaagcggt tgcaaaacgc ttccatcttc cagggatacg acaaggatat   1020
gggctcactg agactacatc agctattctg attacacccg aggggatga taaaccgggc    1080 gcggtcggta agttgttcc attttttgaa gcgaaggttg tggatctgga taccgggaaa    1140
acgctgggcg ttaatcagag aggcgaatta tgtgtcagag acctatgat tatgtccggt    1200 tatgtaaaca atccggaagc gaccaacgcc ttgattgaca aggatggatg ctacattct    1260 ggagacatag cttactggga cgaagacgaa cacttcttca tagttgaccg cttgaagtct   1320
ttaattaaat acaaaggata tcaggtggcc cccgctgaat tggaatcgat attgttacaa   1380 cacccaaca tcttcgacgc gggcgtggca ggtcttcccg acgatgacgc cggtgaactt    1440
cccgccgccg ttgttgtttt ggagcacgga aagacgatga cggaaaaaga gatcgtggat   1500
tacgtcgcca gtcaagtaac aaccgcgaaa aagttgcgcg gaggagttgt gtttgtggac   1560
gaagtaccga aggtcttac cggaaaaactc gacgcaagaa aaatcagaga gatcctcata   1620
aaggccaaga agggcggaaa gtccaaattg taa                                1653

<210> SEQ ID NO 43
<211> LENGTH: 936
<212> TYPE: DNA
<213> ORGANISM: Renilla reniformis

<400> SEQUENCE: 43
atggcttcca aggtgtacga ccccgagcaa cgcaaacgca tgatcactgg gcctcagtgg     60
tgggctcgct gcaagcaaat gaacgtgctg gactccttca tcaactacta tgattccgag    120
aagcacgccg agaacgccgt gatttttctg catggtaacg ctgcctccag ctacctgtgg    180
aggcacgtcg tgcctcacat cgagcccgtg gctagatgca tcatccctga tctgatcgga    240
atgggtaagt ccggcaagag cgggaatggc tcatatcgcc tcctggatca ctacaagtac    300
ctcaccgctt ggttcgagct gctgaacctt ccaaagaaaa tcatctttgt gggccacgac    360 tgggggggctt gtctggcctt tcactactcc tacgagcacc aagacaagat caaggccatc    420
gtccatgctg agagtgtcgt ggacgtgatc gagtcctggg acgagtggcc tgacatcgag    480
gaggatatcg ccctgatcaa gagcgaagag ggcgagaaaa tggtgcttga gaataacttc    540
ttcgtcgaga ccatgctccc aagcaagatc atgcggaaac tggagcctga ggagttcgct    600
gcctacctgg agccattcaa ggagaagggc gaggttagac ggcctaccct ctcctggcct    660
cgcgagatcc ctctcgttaa gggaggcaag cccgacgtcg tccagattgt ccgcaactac    720
aacgcctacc ttcgggccag cgacgatctg cctaagatgt tcatcgagtc cgaccctggg    780
ttcttttcca acgctattgt cgaggagct aagaagttcc ctaacaccga gttcgtgaag    840
gtgaagggcc tccacttcag ccaggaggac gctccagatg aaatgggtaa gtacatcaag    900
agcttcgtgg agcgcgtgct gaagaacgag cagtaa                             936

<210> SEQ ID NO 44
```

-continued

```
<211> LENGTH: 675
<212> TYPE: DNA
<213> ORGANISM: Artificial sequence
<220> FEATURE:
<221> NAME/KEY: misc_feature
<222> LOCATION: (1)..(675)
<223> OTHER INFORMATION: Chimeric transcriptional regulatory expression
      element group (EXP).

<400> SEQUENCE: 44
ggtccgatgt gagacttttc aacaaagggt aatatccgga aacctcctcg gattccattg      60
cccagctatc tgtcacttta ttgtgaagat agtggaaaag gaaggtggct cctacaaatg     120
ccatcattgc gataaaggaa aggccatcgt tgaagatgcc tctgccgaca gtggtcccaa     180
agatggaccc ccacccacga ggagcatcgt ggaaaaagaa gacgttccaa ccacgtcttc     240
aaagcaagtg gattgatgtg atggtccgat gtgagacttt tcaacaaagg gtaatatccg     300
gaaacctcct cggattccat tgcccagcta tctgtcactt tattgtgaag atagtggaaa     360
aggaaggtgg ctcctacaaa tgccatcatt gcgataaagg aaaggccatc gttgaagatg     420
cctctgccga cagtggtccc aaagatggac ccccacccac gaggagcatc gtggaaaaag     480
aagacgttcc aaccacgtct tcaaagcaag tggattgatg tgatatctcc actgacgtaa     540
gggatgacgc acaatcccac tatccttcgc aagacccttc ctctatataa ggaagttcat     600
ttcatttgga gaggaaccat cttccacaca ctcaagccac actattggag aacacacagg     660
gacaacacac cataa                                                     675
```

PLANT REGULATORY ELEMENTS AND USES THEREOF

REFERENCE TO RELATED APPLICATIONS

This application is a divisional of U.S. application Ser. No. 15/449,534, filed Mar. 3, 2017, which application is a divisional of U.S. application Ser. No. 14/207,302, filed Mar. 12, 2014 (now U.S. Pat. No. 9,617,553), which application claims the benefit of U.S. provisional application Ser. No. 61/785,245, filed Mar. 14, 2013, the disclosures of which are incorporated by reference herein in their entirety.

INCORPORATION OF SEQUENCE LISTING

The sequence listing that is contained in the file named "MONS331US.txt," which is 54.4 kilobytes (as measured in Microsoft Windows®) and was created on Mar. 12, 2014, is filed herewith by electronic submission and is incorporated by reference herein.

FIELD OF THE INVENTION

The invention relates to the field of plant molecular biology, plant genetic engineering, and DNA molecules useful for modulating gene expression in plants.

BACKGROUND

Regulatory elements are genetic elements that regulate gene activity by modulating the transcription of an operably linked transcribable DNA molecule. Such elements include promoters, leaders, introns, and 3' untranslated regions, and are useful in the field of plant molecular biology and plant genetic engineering.

SUMMARY OF THE INVENTION

The invention provides novel gene regulatory elements for use in plants and constructs comprising the regulatory elements. The invention also provides transgenic plants, plant cells, plant parts, and seeds comprising the regulatory elements. In one embodiment, the invention provides the regulatory elements disclosed herein operably linked to a transcribable DNA molecule. In certain embodiments, the transcribable DNA molecule is heterologous with respect to a regulatory sequence provided herein. Also provided herein are methods for making and using the regulatory elements disclosed herein, including constructs comprising the regulatory elements, and transgenic plants, plant cells, plant parts, and seeds comprising the regulatory elements operably linked to a transcribable DNA molecule that is heterologous with respect to the regulatory element.

Thus, in one aspect, the invention provides a recombinant DNA molecule comprising a DNA sequence selected from the group consisting of: (a) a DNA sequence with at least about 85 percent sequence identity to any of SEQ ID NOs: 1-20; (b) a DNA sequence comprising any of SEQ ID NOs: 1-20; and (c) a fragment of any of SEQ ID NOs:1-20, wherein the fragment has gene-regulatory activity; wherein the DNA sequence is operably linked to a heterologous transcribable DNA molecule. By "heterologous transcribable DNA molecule," it is meant that the transcribable DNA molecule is heterologous with respect to the DNA sequence. In specific embodiments, the recombinant DNA molecule comprises a DNA sequence having at least about 85 percent, at least about 86 percent at least about 87 percent, at least about 88 percent, at least about 89 percent, at least about 90 percent, at least about 91 percent, at least about 92 percent, at least about 93 percent, at least about 94 percent, at least about 95 percent, at least about 96 percent, at least about 97 percent, at least about 98 percent, or at least about 99 percent sequence identity to the DNA sequence of any of SEQ ID NOs: 1-20. In particular embodiments, the heterologous transcribable DNA molecule comprises a gene of agronomic interest, such as a gene capable of providing herbicide resistance or pest resistance in plants. In still other embodiments, the invention provides a construct comprising a recombinant DNA molecule as provided herein.

In another aspect, provided herein are transgenic plant cells comprising a recombinant DNA molecule comprising a DNA sequence selected from the group consisting of: (a) a DNA sequence with at least about 85 percent sequence identity to any of SEQ ID NOs: 1-20; (b) a DNA sequence comprising any of SEQ ID NOs: 1-20; and (c) a fragment of any of SEQ ID NOs:1-20, wherein the fragment has gene-regulatory activity; wherein the DNA sequence is operably linked to a heterologous transcribable DNA molecule. In certain embodiments, the transgenic plant cell is a monocotyledonous plant cell. In other embodiments, the transgenic plant cell is a dicotyledonous plant cell.

In still yet another aspect, further provided herein is a transgenic plant, or part thereof, comprising a recombinant DNA molecule comprising a DNA sequence selected from the group consisting of: (a) a DNA sequence with at least about 85 percent sequence identity to any of SEQ ID NOs: 1-20; (b) a DNA sequence comprising any of SEQ ID NOs: 1-20; and (c) a fragment of any of SEQ ID NOs: 1-20, wherein the fragment has gene-regulatory activity; wherein the DNA sequence is operably linked to a heterologous transcribable DNA molecule. In specific embodiments, the transgenic plant is a progeny plant of any generation relative to a starting transgenic plant and comprises the recombinant DNA molecule. A transgenic seed comprising the recombinant DNA molecule that produces such a transgenic plant when grown is also provided by the invention.

In another aspect, the invention provides a method of producing a commodity product from a transgenic plant containing the recombinant DNA molecule of the invention. Commodity products of the the invention contain a detectable amount of SEQ ID NOs: 1-20. As used herein, a "commodity product" refers to any composition or product which is comprised of material derived from a transgenic plant, plant part, plant cell, or seed containing the recombinant DNA molecule of the invention. Commodity products include, but are not limited to, processed seeds, grains, plant parts, and meal. Transgenic plants containing the recombinant DNA molecule of the invention can be used to manufacture any commodity product typically acquired from a plant. A commodity product of the invention will contain a detectable amount of DNA corresponding to the recombinant DNA molecule of the invention. Detection of one or more of this recombinant DNA molecule in a sample may be used for determining the content or the source of the commodity product. Any standard method of detection for DNA molecules may be used, including methods of detection disclosed herein.

In still yet another aspect, the invention provides a method of expressing a transcribable DNA molecule, such as a gene of agronomic interest, in a transgenic plant by obtaining a transgenic plant containing a recombinant DNA molecule of the invention and cultivating the plant.

Also provided herein is a method of providing a transgenic plant by transforming a plant cell with a recombinant DNA molecule of the invention to produce a transformed plant cell, and regenerating the transformed plant cell to produce a transgenic plant.

Also provided by the invention is a codon redesigned *Eshericha coli* (*E. coli*) β-glucuronidase (GUS) coding sequence; wherein said codon redesigned GUS coding sequence demonstrates higher expression in a transgenic plant than the native *E. coli* GUS coding sequence. In one embodiment, the codon redesigned GUS coding sequence can be can be selected from the group consisting of SEQ ID NOs: 29 and 30. The transgenic plant may be a monocotyledonous plant. In one embodiment, the monocotyledonous plant is selected from the group consisting of Maize (*Zea mays*), Rice (*Oryza sativa*), Wheat (*Triticum*), Barley (*Hordeum vulgare*), Sorghum (*Sorghum* spp.), Millet, Pearl Millet (*Pennisetum glaucum*), Finger Millet (*Eleusine coracana*), Proso Millet (*Panicum miliaceum*), Foxtail Millet (*Setaria italica*), Oats (*Avena sativa*), Triticale, Rye (*Secale cereale*), Fonio (*Digitaria*), Onions (*Allium* spp.), Pineapple (*Ananas* spp.), Turfgrass, Sugarcane (*Saccharum* spp.), Palm (*Arecaceae*), Bamboo (*Bambuseae*), Banana (*Musaceae*), Ginger family (*Zingiberaceae*), Lilies (*Lilium*), Daffodils (*Narcissus*), Irises (*Iris*), Amaryllis, Orchids (*Orchidaceae*), Cannas, Bluebells (*Hyacinthoides*), and Tulips (*Tulipa*). The transgenic plant may also be a dicotyledonous plant. In one embodiment, the dicotyledonous plant is selected from the group consisting of Soybean (*Glycine max*), Wild Soybean (*Glycine soja*), Cotton (*Gossypium*), Tomato (*Solanum lycopersicum*), Pepper (*Piper*), Squash (*Cucurbita*), Pea (*Pisum sativum*), Alfalfa (*Medicago sativa*), *Medicago truncatula*, Beans (*Phaseolus*), Chick pea (*Cicer arietinum*), Sunflower (*Helianthus annuus*), Potato (*Solanum tuberosum*), Peanut (*Arachis hypogaea*), Quinoa, Buckwheat (*Fagopyrum esculentum*), Carob (*Onia siliqua*), Beet (*Beta vulgaris*), Spinach (*Spinacia oleracea*), and Cucumber (*Cucumis sativus*).

BRIEF DESCRIPTION OF THE FIGURES

FIGS. 1a-1c show an alignment between the native *E. coli* β-glucuronidase (GUS) coding sequence (CR-Ec.uidA-1:1:4, SEQ ID NO: 31) and the codon-redesigned *E. coli* GUS coding sequence (CR-Ec.uidA_nno-1:1:1, SEQ ID NO:30). The identical nucleotides in the alignment are indicated by an asterisk.

BRIEF DESCRIPTION OF THE SEQUENCES

SEQ ID NOs: 1, 3, 5, 7, 9, 11, 13, 15, 17, 19, 21, and 23 are promoter sequences.

SEQ ID NOs: 2, 4, 6, 8, 10, 12, 14, 16, 18, 20, 22 and 24 are leader sequences.

SEQ ID NOs: 25-28 are amplification primer sequences.

SEQ ID NOs: 29 and 30 are codon redesigned GUS coding sequences. SEQ ID NO: 29 comprises a processable intron, while SEQ ID NO: 30 is a contiguous coding sequence.

SEQ ID NO: 31 is the native *Escherichia coli* β-glucuronidase coding sequence.

SEQ ID NO: 32 is a GUS coding sequence with a processable intron based upon the native *E. coli* β-glucuronidase of SEQ ID NO: 31.

SEQ ID NOs: 33, 39 and 40 are 3' UTR sequences.

SEQ ID NOs: 34-37, 41 and 44 are sequences of transcriptional regulatory expression element groups (EXPs) comprising either a promoter sequence operably linked 5' to a leader sequence which is operably linked 5' to a to an intron sequence, or in the case of SEQ ID 44, a promoter sequence operably linked 5' to a leader sequence.

SEQ ID NO: 38 is an intron sequence.

SEQ ID NOs: 42 and 44 are coding sequences for luciferase proteins derived from *Photinus pyralis* and *Renilla reniformis*, respectively.

DETAILED DESCRIPTION OF THE INVENTION

The invention provides DNA molecules having gene-regulatory activity in plants. The nucleotide sequences of these DNA molecules are provided as SEQ ID NOs: 1-20. These DNA molecules are, for instance, capable of affecting the expression of an operably linked transcribable DNA molecule in plant tissues, and therefore regulating gene expression of an operably linked transgene in transgenic plants. The invention also provides methods of modifying, producing, and using the same. The invention also provides compositions that include transgenic plant cells, plants, plant parts, and seeds containing recombinant DNA molecules of the invention, and methods for preparing and using the same.

The following definitions and methods are provided to better define the present invention and to guide those of ordinary skill in the art in the practice of the invention. Unless otherwise noted, terms are to be understood according to conventional usage by those of ordinary skill in the relevant art.

DNA Molecules

As used herein, the term "DNA" or "DNA molecule" refers to a double-stranded DNA molecule of genomic or synthetic origin, i.e., a polymer of deoxyribonucleotide bases. As used herein, the term "DNA sequence" refers to the nucleotide sequence of a DNA molecule. The nomenclature used herein corresponds to that of Title 37 of the United States Code of Federal Regulations § 1.822, and set forth in the tables in WIPO Standard ST.25 (1998), Appendix 2, Tables 1 and 3.

As used herein, a "recombinant DNA molecule" is a DNA molecule comprising a combination of DNA molecules that would not naturally occur together without human intervention. For instance, a recombinant DNA molecule may be a DNA molecule that is comprised of at least two DNA molecules heterologous with respect to each other, a DNA molecule that comprises a DNA sequence that deviates from DNA sequences that exist in nature, or a DNA molecule that has been incorporated into a host cell's DNA by genetic transformation.

As used herein, the term "sequence identity" refers to the extent to which two optimally aligned polynucleotide sequences or two optimally aligned polypeptide sequences are identical. An optimal sequence alignment is created by manually aligning two sequences, e.g., a reference sequence and another DNA sequence, to maximize the number of nucleotide matches in the sequence alignment with appropriate internal nucleotide insertions, deletions, or gaps. As used herein, the term "reference sequence" refers to a DNA sequence provided as SEQ ID NOs: 1-20.

As used herein, the term "percent sequence identity" or "percent identity" or "% identity" is the identity fraction multiplied by 100. The "identity fraction" for a sequence optimally aligned with a reference sequence is the number of nucleotide matches in the optimal alignment, divided by the total number of nucleotides in the reference sequence, e.g., the total number of nucleotides in the full length of the entire reference sequence. Thus, one embodiment of the invention provides a DNA molecule comprising a sequence that when optimally aligned to a reference sequence, provided herein as SEQ ID NOs: 1-20, has at least about 85 percent identity, at least about 86 percent identity, at least about 87 percent identity, at least about 88 percent identity at least about 89 percent identity, at least about 90 percent identity, at least about 91 percent identity, at least about 92 percent identity, at least about 93 percent identity, at least about 94 percent identity, at least about 95 percent identity, at least about 96 percent identity, at least about 97 percent identity, at least about 98 percent identity, at least about 99 percent identity, or at least about 100 percent identity to the reference sequence.

Regulatory Elements

Regulatory elements such as promoters, leaders, enhancers, introns, and transcription termination regions (or 3' UTRs) play an integral part in the overall expression of genes in living cells. The term "regulatory element," as used herein, refers to a DNA molecule having gene-regulatory activity. The term "gene-regulatory activity," as used herein, refers to the ability to affect the expression of an operably linked transcribable DNA molecule, for instance by affecting the transcription and/or translation of the operably linked transcribable DNA molecule. Regulatory elements, such as promoters, leaders, enhancers, introns and 3' UTRs that function in plants are therefore useful for modifying plant phenotypes through genetic engineering.

As used herein, a "regulatory expression element group" or "EXP" sequence may refer to a group of operably linked regulatory elements, such as enhancers, promoters, leaders, and introns. Thus, a regulatory expression element group may be comprised, for instance, of a promoter operably linked 5' to a leader sequence, which is in turn operably linked 5' to an intron sequence.

Regulatory elements may be characterized by their gene expression pattern, e.g., positive and/or negative effects such as constitutive expression or temporal, spatial, developmental, tissue, environmental, physiological, pathological, cell cycle, and/or chemically responsive expression, and any combination thereof, as well as by quantitative or qualitative indications. As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a double-stranded RNA (dsRNA), a transfer RNA (tRNA), a ribosomal RNA (rRNA), a microRNA (miRNA), and the like.

As used herein, the term "protein expression" is any pattern of translation of a transcribed RNA molecule into a protein molecule. Protein expression may be characterized by its temporal, spatial, developmental, or morphological qualities, as well as by quantitative or qualitative indications.

A promoter is useful as a regulatory element for modulating the expression of an operably linked transcribable DNA molecule. As used herein, the term "promoter" refers generally to a DNA molecule that is involved in recognition and binding of RNA polymerase II and other proteins, such as trans-acting transcription factors, to initiate transcription. A promoter may originate from the 5' untranslated region (5' UTR) of a gene. Alternately, promoters may be synthetically produced or manipulated DNA molecules. Promoters may also be chimeric. Chimeric promoters are produced through the fusion of two or more heterologous DNA molecules. Promoters useful in practicing the present invention include SEQ ID NOs: 1, 3, 5, 7, 9, 11, 13, 15, 17, and 19, including fragments or variants thereof. In specific embodiments of the invention, such DNA molecules and any variants or derivatives thereof as described herein, may be further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" that provides a basal level of transcription and is comprised of a TATA box or equivalent DNA sequence for recognition and binding of the RNA polymerase II complex for initiation of transcription.

In one embodiment, fragments of a promoter sequence disclosed herein are provided. Promoter fragments may comprise promoter activity, as described above, and may be useful alone or in combination with other promoters and promoter fragments, such as in constructing chimeric promoters. In specific embodiments, fragments of a promoter are provided comprising at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 900, or at least about 1000 contiguous nucleotides, or longer, of a polynucleotide molecule having promoter activity disclosed herein. Methods for producing such fragments from a starting promoter molecule are well known in the art.

Compositions derived from any of the promoters presented as SEQ ID NOs: 1, 3, 5, 7, 9, 11, 13, 15, 17, and 19, such as internal or 5' deletions, for example, can be produced using methods known in the art to improve or alter expression, including by removing elements that have either positive or negative effects on expression, duplicating elements that have positive or negative effects on expression, and/or duplicating or removing elements that have tissue- or cell-specific effects on expression. Compositions derived from any of the promoters presented as SEQ ID NOs: 1, 3, 5, 7, 9, 11, 13, 15, 17, and 19 comprised of 3' deletions in which the TATA box element or equivalent sequence thereof and downstream sequence is removed can be used, for example, to make enhancer elements. Further deletions can be made to remove any elements that have positive or negative; tissue-specific; cell-specific; or timing-specific (such as, but not limited to, circadian rhythm) effects on expression. Any of the promoters presented as SEQ ID NOs: 1, 3, 5, 7, 9, 11, 13, 15, 17, and 19 and fragments or enhancers derived therefrom can be used to make chimeric transcriptional regulatory element compositions comprised of any of the promoters presented as SEQ ID NOs:1, 3, 5, 7, 9, 11, 13, 15, 17, and 19 and the fragments or enhancers derived therefrom operably linked to other enhancers and promoters.

In accordance with the invention, a promoter or promoter fragment may be analyzed for the presence of known promoter elements, i.e., DNA sequence characteristics, such as a TATA box and other known transcription factor binding site motifs. Identification of such known promoter elements may be used by one of skill in the art to design variants of the promoter having a similar expression pattern to the original promoter.

As used herein, the term "leader" refers to a DNA molecule from the untranslated 5' region (5' UTR) of a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable DNA molecule. Leader molecules may be used with a heterologous promoter or with their native promoter. Promoter molecules of the present invention may thus be operably linked to their native leader or may be operably linked to a heterologous leader. Leaders useful in practicing the invention include SEQ ID NOs: 2, 4, 6, 8, 10, 12, 14, 16, 18, and 20 or fragments or variants thereof. In specific embodiments, such DNA sequences may be defined as being capable of acting as a leader in a host cell, including, for example, a transgenic plant cell. In one embodiment, such DNA sequences are decoded as comprising leader activity.

The leader sequences (5' UTR) presented as SEQ ID NOs: 2, 4, 6, 8, 10, 12, 14, 16, 18, and 20 may be comprised of regulatory elements or may adopt secondary structures that can have an effect on transcription or translation of an operably linked DNA molecule. The leader sequences presented as SEQ ID NOs: 2, 4, 6, 8, 10, 12, 14, 16, 18, and 20 can be used in accordance with the invention to make chimeric regulatory elements that affect transcription or translation of an operably linked DNA molecule. In addition, the leader sequences presented as SEQ ID NOs: 2, 4, 6, 8, 10, 12, 14, 16, 18, and 20 can be used to make chimeric leader sequences that affect transcription or translation of an operably linked DNA molecule.

As used herein, the term "intron" refers to a DNA molecule that may be identified from a gene and may be defined generally as a region spliced out during messenger RNA (mRNA) processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable DNA molecule. A construct may comprise an intron, and the intron may or may not be heterologous with respect to the transcribable DNA molecule. Examples of introns in the art include the rice actin intron and the corn HSP70 intron.

In plants, the inclusion of some introns in gene constructs leads to increased mRNA and protein accumulation relative to constructs lacking the intron. This effect has been termed "intron mediated enhancement" (IME) of gene expression (Mascarenhas et al., *Plant Mol. Biol.* 15:913-920, 1990). Introns known to stimulate expression in plants have been identified in maize genes (e.g., tubA1, Adh1, Sh1, and Ubi1), in rice genes (e.g., tpi) and in dicotyledonous plant genes like those from *petunia* (e.g., rbcS), potato (e.g., st-ls1) and from *Arabidopsis thaliana* (e.g., ubq3 and pat1). It has been shown that deletions or mutations within the splice sites of an intron reduce gene expression, indicating that splicing might be needed for IME. However, splicing per se might not be required, as IME in dicotyledonous plants has been shown by point mutations within the splice sites of the pat1 gene from *A. thaliana*. Multiple uses of the same intron in one plant has been shown to exhibit disadvantages. In those cases, it is necessary to have a collection of basic control elements for the construction of appropriate recombinant DNA elements.

As used herein, the term "3' transcription termination molecule," "3' untranslated region" or "3' UTR" herein refers to a DNA molecule that is used during transcription to the untranslated region of the 3' portion of an mRNA molecule. The 3' untranslated region of an mRNA molecule may be generated by specific cleavage and 3' polyadenylation, also known as a polyA tail. A 3' UTR may be operably linked to and located downstream of a transcribable DNA molecule and may include a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region; wheat hsp17 3' region, pea rubisco small subunit 3' region, cotton E6 3' region, and the coixin 3' UTR.

3' UTRs typically find beneficial use for the recombinant expression of specific DNA molecules. A weak 3' UTR has the potential to generate read-through, which may affect the expression of the DNA molecule located in the neighboring expression cassettes. Appropriate control of transcription termination can prevent read-through into DNA sequences (e.g., other expression cassettes) localized downstream and can further allow efficient recycling of RNA polymerase to improve gene expression. Efficient termination of transcription (release of RNA polymerase II from the DNA) is prerequisite for re-initiation of transcription and thereby directly affects the overall transcript level. Subsequent to transcription termination, the mature mRNA is released from the site of synthesis and template transported to the cytoplasm. Eukaryotic mRNAs are accumulated as poly(A) forms in vivo, making it difficult to detect transcriptional termination sites by conventional methods. Further, prediction of functional and efficient 3' UTRs by bioinformatics methods is difficult in that there are no conserved DNA sequences that would allow easy prediction of an effective 3' UTR.

From a practical standpoint, it is typically beneficial that a 3' UTR used in an expression cassette possesses the following characteristics. The 3' UTR should be able to efficiently and effectively terminate transcription of the transcribable DNA molecule and prevent read-through of the transcript into any neighboring DNA sequence, which can be comprised of another expression cassette as in the case of multiple expression cassettes residing in one transfer DNA (T-DNA), or the neighboring chromosomal DNA into which the T-DNA has inserted. The 3' UTR should not cause a reduction in the transcriptional activity imparted by the promoter, leader, enhancers, and introns that are used to drive expression of the DNA molecule. In plant biotechnology, the 3' UTR is often used for priming of amplification reactions of reverse transcribed RNA extracted from the transformed plant and used to: (1) assess the transcriptional activity or expression of the expression cassette once integrated into the plant chromosome; (2) assess the copy number of insertions within the plant DNA; and (3) assess zygosity of the resulting seed after breeding. The 3' UTR is also used in amplification reactions of DNA extracted from the transformed plant to characterize the intactness of the inserted cassette.

As used herein, the term "enhancer" or "enhancer element" refers to a cis-acting regulatory element, a.k.a. cis-element, which confers an aspect of the overall expression pattern, but is usually insufficient alone to drive transcription of an operably linked DNA sequence. Unlike promoters, enhancer elements do not usually include a transcription start site (TSS) or TATA box or equivalent DNA sequence. A promoter or promoter fragment may naturally comprise one or more enhancer elements that affect the transcription of an operably linked DNA sequence. An enhancer element may also be fused to a promoter to produce a chimeric promoter cis-element, which confers an aspect of the overall modulation of gene expression.

Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated polymerase chain reaction (PCR), and other conventional assays; or by DNA sequence similarity analysis using known cis-element motifs or enhancer elements as a target sequence or target motif with conventional DNA sequence comparison methods, such as the Basic Alignment Search Tool (BLAST®). The fine structure of an enhancer domain can be further studied by mutagenesis (or substitution) of one or more nucleotides or by other conventional methods known in the art. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable DNA molecules are encompassed by the invention.

As used herein, the term "chimeric" refers to a single DNA molecule produced by fusing a first DNA molecule to a second DNA molecule, where neither the first nor the second DNA molecule would normally be found in that configuration, i.e., fused to the other. The chimeric DNA molecule is thus a new DNA molecule not otherwise normally contained in nature. As used herein, the term "chimeric promoter" refers to a promoter produced through such manipulation of DNA molecules. A chimeric promoter may combine two or more DNA fragments, for example, the fusion of a promoter to an enhancer element. Thus, the design, construction, and use of chimeric promoters according to the methods disclosed herein for modulating the expression of operably linked transcribable polynucleotide molecules are encompassed by the invention.

As used herein, the term "variant" refers to a second DNA molecule, such as a regulatory element, that is similar in composition, but not identical to, a first DNA molecule, and wherein the second DNA molecule still maintains the general functionality, i.e., the same or similar expression pattern, of the first DNA molecule. A variant may be a shortened or truncated version of the first DNA molecule and/or an altered version of the DNA sequence of the first DNA molecule, such as one with different restriction enzyme sites and/or internal deletions, substitutions, and/or insertions. Regulatory element "variants" also encompass variants arising from mutations that naturally occur in bacterial and plant cell transformation. In the invention, a DNA sequence provided as SEQ ID NOs: 1-20 may be used to create variants that are similar in composition, but not identical to, the DNA sequence of the original regulatory element, while still maintaining the general functionality, i.e., the same or similar expression pattern, of the original regulatory element. Production of such variants of the invention is well within the ordinary skill of the art in light of the disclosure and is encompassed within the scope of the invention.

Chimeric regulatory elements can be designed to comprise various constituent elements which may be operatively linked by various methods known in the art, such as restriction enzyme digestion and ligation, ligation independent cloning, modular assembly of PCR products during amplification, or direct chemical synthesis of the regulatory element, as well as other methods known in the art. The resulting various chimeric regulatory elements can be comprised of the same, or variants of the same, constituent elements but differ in the DNA sequence or DNA sequences that comprise the linking DNA sequence or sequences that allow the constituent parts to be operatively linked. In the invention, a DNA sequence provided as SEQ ID NOs: 1-20 may provide a regulatory element reference sequence, wherein the constituent elements that comprise the reference sequence may be joined by methods known in the art and may comprise substitutions, deletions, and/or insertions of one or more nucleotides or mutations that naturally occur in bacterial and plant cell transformation.

The efficacy of the modifications, duplications, or deletions described herein on the desired expression aspects of a particular transgene may be tested empirically in stable and transient plant assays, such as those described in the working examples herein, so as to validate the results, which may vary depending upon the changes made and the goal of the change in the starting DNA molecule.

Constructs

As used herein, the term "construct" means any recombinant DNA molecule such as a plasmid, cosmid, virus, phage, or linear or circular DNA or RNA molecule, derived from any source, capable of genomic integration or autonomous replication, comprising a DNA molecule where at least one DNA molecule has been linked to another DNA molecule in a functionally operative manner, i.e., operably linked. As used herein, the term "vector" means any construct that may be used for the purpose of transformation, i.e., the introduction of heterologous DNA or RNA into a host cell. A construct typically includes one or more expression cassettes. As used herein, an "expression cassette" refers to a DNA molecule comprising at least a transcribable DNA molecule operably linked to one or more regulatory elements, typically at least a promoter and a 3' UTR.

As used herein, the term "operably linked" refers to a first DNA molecule joined to a second DNA molecule, wherein the first and second DNA molecules are so arranged that the first DNA molecule affects the function of the second DNA molecule. The two DNA molecules may or may not be part of a single contiguous DNA molecule and may or may not be adjacent. For example, a promoter is operably linked to a transcribable DNA molecule if the promoter modulates transcription of the transcribable DNA molecule of interest in a cell. A leader, for example, is operably linked to DNA sequence when it is capable of affecting the transcription or translation of the DNA sequence.

The constructs of the invention may be provided, in one embodiment, as double tumor-inducing (Ti) plasmid border constructs that have the right border (RB or AGRtu.RB) and left border (LB or AGRtu.LB) regions of the Ti plasmid isolated from *Agrobacterium tumefaciens* comprising a T-DNA that, along with transfer molecules provided by the *A. tumefaciens* cells, permit the integration of the T-DNA into the genome of a plant cell (see, e.g., U.S. Pat. No. 6,603,061). The constructs may also contain the plasmid backbone DNA segments that provide replication function and antibiotic selection in bacterial cells, e.g., an *Escherichia coli* origin of replication such as ori322, a broad host range origin of replication such as oriV or oriRi, and a coding region for a selectable marker such as Spec/Strp that encodes for Tn7 aminoglycoside adenyltransferase (*aadA*) conferring resistance to spectinomycin or streptomycin, or a gentamicin (Gm, Gent) selectable marker gene. For plant transformation, the host bacterial strain is often *A. tumefaciens* ABI, C58, or LBA4404; however, other strains known to those skilled in the art of plant transformation can function in the invention.

Methods are known in the art for assembling and introducing constructs into a cell in such a manner that the transcribable DNA molecule is transcribed into a functional mRNA molecule that is translated and expressed as a protein. For the practice of the invention, conventional compositions and methods for preparing and using constructs and host cells are well known to one skilled in the art. Typical vectors useful for expression of nucleic acids in higher plants are well known in the art and include vectors derived from the Ti plasmid of *Agrobacterium tumefaciens* and the pCaMVCN transfer control vector.

Various regulatory elements may be included in a construct, including any of those provided herein. Any such regulatory elements may be provided in combination with other regulatory elements. Such combinations can be designed or modified to produce desirable regulatory features. In one embodiment, constructs of the invention comprise at least one regulatory element operably linked to a transcribable DNA molecule operably linked to a 3' UTR.

Constructs of the invention may include any promoter or leader provided herein or known in the art. For example, a promoter of the invention may be operably linked to a heterologous non-translated 5' leader such as one derived from a heat shock protein gene. Alternatively, a leader of the invention may be operably linked to a heterologous promoter such as the Cauliflower Mosaic Virus 35S transcript promoter.

Expression cassettes may also include a transit peptide coding sequence that encodes a peptide that is useful for sub-cellular targeting of an operably linked protein, particularly to a chloroplast, leucoplast, or other plastid organelle; mitochondria; peroxisome; vacuole; or an extracellular location. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, and enolpyruvyl shikimate phosphate synthase (EPSPS). Chloroplast transit peptides are described, for example, in U.S. Pat. No. 7,193,133. It has been demonstrated that non-chloroplast proteins may be targeted to the chloroplast by the expression of a heterologous CTP operably linked to the transgene encoding non-chloroplast proteins.

Transcribable DNA Molecules

As used herein, the term "transcribable DNA molecule" refers to any DNA molecule capable of being transcribed into a RNA molecule, including, but not limited to, those having protein coding sequences and those producing RNA molecules having sequences useful for gene suppression. The type of DNA molecule can include, but is not limited to, a DNA molecule from the same plant, a DNA molecule from another plant, a DNA molecule from a different organism, or a synthetic DNA molecule, such as a DNA molecule containing an antisense message of a gene, or a DNA molecule encoding an artificial, synthetic, or otherwise modified version of a transgene. Exemplary transcribable DNA molecules for incorporation into constructs of the invention include, e.g., DNA molecules or genes from a species other than the species into which the DNA molecule is incorporated or genes that originate from, or are present in, the same species but are incorporated into recipient cells by genetic engineering methods rather than classical breeding techniques.

A "transgene" refers to a transcribable DNA molecule heterologous to a host cell at least with respect to its location in the host cell genome and/or a transcribable DNA molecule artificially incorporated into a host cell's genome in the current or any prior generation of the cell.

A regulatory element, such as a promoter of the invention, may be operably linked to a transcribable DNA molecule that is heterologous with respect to the regulatory element. As used herein, the term "heterologous" refers to the combination of two or more DNA molecules when such a combination is not normally found in nature. For example, the two DNA molecules may be derived from different species and/or the two DNA molecules may be derived from different genes, e.g., different genes from the same species or the same genes from different species. A regulatory element is thus heterologous with respect to an operably linked transcribable DNA molecule if such a combination is not normally found in nature, i.e., the transcribable DNA molecule does not naturally occur operably linked to the regulatory element.

The transcribable DNA molecule may generally be any DNA molecule for which expression of a transcript is desired. Such expression of a transcript may result in translation of the resulting mRNA molecule, and thus protein expression. Alternatively, for example, a transcribable DNA molecule may be designed to ultimately cause decreased expression of a specific gene or protein. In one embodiment, this may be accomplished by using a transcribable DNA molecule that is oriented in the antisense direction. One of ordinary skill in the art is familiar with using such antisense technology. Any gene may be negatively regulated in this manner, and, in one embodiment, a transcribable DNA molecule may be designed for suppression of a specific gene through expression of a dsRNA, siRNA or miRNA molecule.

Thus, one embodiment of the invention is a recombinant DNA molecule comprising a regulatory element of the invention, such as those provided as SEQ ID NOs: 1-20, operably linked to a heterologous transcribable DNA molecule so as to modulate transcription of the transcribable DNA molecule at a desired level or in a desired pattern when the construct is integrated in the genome of a transgenic plant cell. In one embodiment, the transcribable DNA molecule comprises a protein-coding region of a gene and in another embodiment the transcribable DNA molecule comprises an antisense region of a gene.

Genes of Agronomic Interest

A transcribable DNA molecule may be a gene of agronomic interest. As used herein, the term "gene of agronomic interest" refers to a transcribable DNA molecule that, when expressed in a particular plant tissue, cell, or cell type, confers a desirable characteristic. The product of a gene of agronomic interest may act within the plant in order to cause an effect upon the plant morphology, physiology, growth, development, yield, grain composition, nutritional profile, disease or pest resistance, and/or environmental or chemical tolerance or may act as a pesticidal agent in the diet of a pest that feeds on the plant. In one embodiment of the invention, a regulatory element of the invention is incorporated into a construct such that the regulatory element is operably linked to a transcribable DNA molecule that is a gene of agronomic interest. In a transgenic plant containing such a construct, the expression of the gene of agronomic interest can confer a beneficial agronomic trait. A beneficial agronomic trait may include, but is not limited to, herbicide tolerance, insect control, modified yield, disease resistance, pathogen resistance, modified plant growth and development, modified starch content, modified oil content, modified fatty acid content, modified protein content, modified fruit ripening, enhanced animal and human nutrition, biopolymer productions, environmental stress resistance, pharmaceutical peptides, improved processing qualities, improved flavor, hybrid seed production utility, improved fiber production, and desirable biofuel production.

Examples of genes of agronomic interest known in the art include those for herbicide resistance (U.S. Pat. Nos. 6,803, 501; 6,448,476; 6,248,876; 6,225,114; 6,107,549; 5,866, 775; 5,804,425; 5,633,435; and 5,463,175), increased yield (U.S. Pat. Nos. USRE38,446; 6,716,474; 6,663,906; 6,476, 295; 6,441,277; 6,423,828; 6,399,330; 6,372,211; 6,235, 971; 6,222,098; and 5,716,837), insect control (U.S. Pat. Nos. 6,809,078; 6,713,063; 6,686,452; 6,657,046; 6,645, 497; 6,642,030; 6,639,054; 6,620,988; 6,593,293; 6,555, 655; 6,538,109; 6,537,756; 6,521,442; 6,501,009; 6,468, 523; 6,326,351; 6,313,378; 6,284,949; 6,281,016; 6,248, 536; 6,242,241; 6,221,649; 6,177,615; 6,156,573; 6,153, 814; 6,110,464; 6,093,695; 6,063,756; 6,063,597; 6,023, 013; 5,959,091; 5,942,664; 5,942,658; 5,880,275; 5,763, 245; and 5,763,241), fungal disease resistance (U.S. Pat. Nos. 6,653,280; 6,573,361; 6,506,962; 6,316,407; 6,215, 048; 5,516,671; 5,773,696; 6,121,436; 6,316,407; and 6,506,962), virus resistance (U.S. Pat. Nos. 6,617,496; 6,608,241; 6,015,940; 6,013,864; 5,850,023; and 5,304, 730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; 6,476,295), modified oils production (U.S. Pat. Nos. 6,444,876; 6,426,447; and 6,380, 462), high oil production (U.S. Pat. Nos. 6,495,739; 5,608, 149; 6,483,008; and 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; and 6,459,018), high protein production (U.S. Pat. No. 6,380, 466), fruit ripening (U.S. Pat. No. 5,512,466), enhanced animal and human nutrition (U.S. Pat. Nos. 6,723,837; 6,653,530; 6,5412,59; 5,985,605; and 6,171,640), biopolymers (U.S. Pat. Nos. USRE37,543; 6,228,623; and 5,958, 745, and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229, 114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998, 700).

Alternatively, a gene of agronomic interest can affect the above mentioned plant characteristics or phenotypes by encoding a RNA molecule that causes the targeted modulation of gene expression of an endogenous gene, for example by antisense (see, e.g., U.S. Pat. No. 5,107,065); inhibitory RNA ("RNAi," including modulation of gene expression by miRNA-, siRNA-, trans-acting siRNA-, and phased sRNA-mediated mechanisms, e.g., as described in published applications U.S. 2006/0200878 and U.S. 2008/0066206, and in U.S. patent application Ser. No. 11/974,469); or cosuppression-mediated mechanisms. The RNA could also be a catalytic RNA molecule (e.g., a ribozyme or a riboswitch; see, e.g., U.S. 2006/0200878) engineered to cleave a desired endogenous mRNA product. Methods are known in the art for constructing and introducing constructs into a cell in such a manner that the transcribable DNA molecule is transcribed into a molecule that is capable of causing gene suppression.

Expression of a transcribable DNA molecule in a plant cell can also be used to suppress plant pests feeding on the plant cell, for example, compositions isolated from coleopteran pests and compositions isolated from nematode pests. Plant pests include, but are not limited to, arthropod pests, nematode pests, and fungal or microbial pests.

Selectable Markers

Selectable marker transgenes may also be used with the regulatory elements of the invention. As used herein the term "selectable marker transgene" refers to any transcribable DNA molecule whose expression in a transgenic plant, tissue or cell, or lack thereof, can be screened for or scored in some way. Selectable marker genes, and their associated selection and screening techniques, for use in the practice of the invention are known in the art and include, but are not limited to, transcribable DNA molecules encoding ß-glucuronidase (GUS), green fluorescent protein (GFP), proteins that confer antibiotic resistance, and proteins that confer herbicide tolerance.

β-Glucuronidase

The β-glucuronidase (GUS) gene isolated from *Escherichia coli* K-12 is one of the most widely used report genes in plant biotechnology. The *E. coli* GUS gene, uidA, is part of the GUS operon on the bacterial chromosome. It is induced by a wide variety of β-D-glucuronides. The GUS enzyme is an exohydrolase that catalyses the hydrolysis of β-D-glucuronides into D-glucuronic acid and the aglycone. *E. coli* lives in the digestive tract of vertebrates, including man. Vertebrates utilize the glucuronidation pathway to detoxify xenobiotics and endogenous waste compounds such as steroids, aliphatic alcohols, phenol, carboxylic acids, sugars, and various other metabolites. Glucuronidation involves conjugation with D-glucuronic acid. This occurs mainly in the liver, but also occurs in other tissues and organs such as the kidney, the adrenal glands, and the alimentary tract. The glucuronic acid can be utilized by *E. coli* as a main source for carbon and energy. The *E. coli* GUS protein therefore provides a means by which the bacterium can degrade the products of the glucuronidation pathway in the alimentary tract of vertebrates to yield glucuronic acid as a carbon and energy source. The aglycones that are also liberated by the GUS enzyme are generally not degraded by the bacterium, but utilized as a shuttle for D-glucuronic acid (Gilissen et al., *Transgenic Research,* 7: 157-163, 1998).

The use of the *E. coli* β-glucuronidase gene as a reporter was first described by Jefferson et al. (*Proc. Natl. Acad. Sci.,* 83: 8447-8451, 1986) and has been used in much the same manner as first described since its introduction. The GUS gene is used to monitor plant gene expression and is frequently employed to characterize promoters or other expression elements. However, some plant promoters express at very low levels and may be undetectable using a GUS-based assay. These lower expressing promoters may be valuable to the development of transgenic crops with desirable phenotypes such as improved yield.

Early on in the development of transgenic crop plants, promoters that provided high constitutive expression were most desired. These high constitutive promoters, derived from plant viral genomes such as Cauliflower mosaic virus and Figwort mosaic virus, were used to drive transgenes that conferred herbicide tolerance or insect resistance. As the field of plant biotechnology increases in complexity, newer transgenic traits are being developed that require more specific patterns of expression or lower levels of expression. Overexpression or expression in the wrong plant tissues can lead to unwanted effects in the transformed plant. For example, ectopic expression (expression of a gene in an abnormal place in an organism) of enzyme genes in plants can result in a reduction in the desired end product due to a shortage of precursor at the branching point in a metabolic pathway (Iwase et al., *Plant Biotech.* 26: 29-38, 2009).

Because transcription factors (TFs) naturally act as master regulators of cellular processes, they are expected to be excellent candidates for modifying complex traits in crop plants, and TF-based technologies are likely to be a prominent part of the next generation of successful biotechnology crops. TF technologies often require optimization, either to reduce unwanted side effects such as growth retardation or to enhance the desired trait to the level at which it is of commercial value. Optimization is frequently approached by modifying expression of the TF transgene. Tissue-specific, developmental, or inducible promoters, rather than the usual constitutive promoters, can be utilized to limit expression of the transgene to the appropriate tissues or environmental conditions (Century et al., *Plant Physiology,* 147: 20-29, 2008).

Due in part to these developments, there is a need for a more sensitive assay for expression element characterization to identify expression elements that provide a desired level and pattern of expression. The present invention provides an improved, codon redesigned GUS coding sequence which, when operably linked to a promoter, expresses better than the native *E. coli* GUS coding sequence used commonly in the art. This improved, codon redesigned GUS coding sequence can be used to provide greater assay sensitivity, both quantitatively and qualitatively, and allows for the characterization of promoters and other expression elements that might otherwise not be possible with the native *E. coli* GUS coding sequence. The improved, codon redesigned GUS coding sequence can be used to characterize expression elements in monocot and dicot plants. Monocot plants useful in practicing the invention include, but are not limited to, Maize (*Zea mays*), Rice (*Oryza sativa*), Wheat (*Triticum*), Barley (*Hordeum vulgare*), Sorghum (*Sorghum* spp.), Millet, Pearl Millet (*Pennisetum glaucum*), Finger Millet (*Eleusine coracana*), Proso Millet (*Panicum miliaceum*), Foxtail Millet (*Setaria italica*), Oats (*Avena sativa*), Triticale, Rye (*Secale cereale*), Fonio (*Digitaria*), Onions (*Allium* spp.), Pineapple (*Ananas* spp.), Turfgrass, Sugarcane (*Saccharum* spp.), Palm (*Arecaceae*), Bamboo (*Bambuseae*), Banana (*Musaceae*), Ginger family (*Zingiberaceae*), Lilies (*Lilium*), Daffodils (*Narcissus*), Irises (*Iris*), Amaryllis, Orchids (*Orchidaceae*), Cannas, Bluebells (*Hyacinthoides*) and Tulips (*Tulipa*). Dicot plants useful in practicing the invention include, but are not limited to, Soybean (*Glycine max*), Wild Soybean (*Glycine soja*), Cotton (*Gossypium*), Tomato (*Solanum lycopersicum*), Pepper (*Piper*), Squash (*Cucurbita*), Pea (*Pisum sativum*), Alfalfa (*Medicago sativa*), *Medicago truncatula,* Beans (*Phaseolus*), Chick pea (*Cicer arietinum*), Sunflower (*Helianthus annuus*), Potato (*Solanum tuberosum*), Peanut (*Arachis hypogaea*), Quinoa, Buckwheat (*Fagopyrum esculentum*), Carob (*Onia siliqua*), Beet (*Beta vulgaris*), Spinach (*Spinacia oleracea*), and Cucumber (*Cucumis sativus*).

Cell Transformation

The invention is also directed to a method of producing transformed cells and plants that comprise one or more regulatory elements operably linked to a transcribable DNA molecule.

The term "transformation" refers to the introduction of a DNA molecule into a recipient host. As used herein, the term "host" refers to bacteria, fungi, or plants, including any cells, tissues, organs, or progeny of the bacteria, fungi, or plants. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign DNA molecule, such as a construct, has been introduced. The introduced DNA molecule may be integrated into the genomic DNA of the recipient cell, tissue, organ, or organism such that the introduced DNA molecule is inherited by subsequent progeny. A "transgenic" or "transformed" cell or organism may also includes progeny of the cell or organism and progeny produced from a breeding program employing such a transgenic organism as a parent in a cross and exhibiting an altered phenotype resulting from the presence of a foreign DNA molecule. The introduced DNA molecule may also be transiently introduced into the recipient cell such that the introduced DNA molecule is not inherited by subsequent progeny. The term "transgenic" refers to a bacterium, fungus, or plant containing one or more heterologous DNA molecules.

There are many methods well known to those of skill in the art for introducing DNA molecules into plant cells. The process generally comprises the steps of selecting a suitable host cell, transforming the host cell with a vector, and obtaining the transformed host cell. Methods and materials for transforming plant cells by introducing a construct into a plant genome in the practice of this invention can include any of the well-known and demonstrated methods. Suitable methods include, but are not limited to, bacterial infection (e.g., *Agrobacterium*), binary BAC vectors, direct delivery of DNA (e.g., by PEG-mediated transformation, desiccation/inhibition-mediated DNA uptake, electroporation, agitation with silicon carbide fibers, and acceleration of DNA coated particles), among others.

Host cells may be any cell or organism, such as a plant cell, algal cell, algae, fungal cell, fungi, bacterial cell, or insect cell. In specific embodiments, the host cells and transformed cells may include cells from crop plants.

A transgenic plant subsequently may be regenerated from a transgenic plant cell of the invention. Using conventional breeding techniques or self-pollination, seed may be produced from this transgenic plant. Such seed, and the resulting progeny plant grown from such seed, will contain the recombinant DNA molecule of the invention, and therefore will be transgenic.

Transgenic plants of the invention can be self-pollinated to provide seed for homozygous transgenic plants of the invention (homozygous for the recombinant DNA molecule) or crossed with non-transgenic plants or different transgenic plants to provide seed for heterozygous transgenic plants of the invention (heterozygous for the recombinant DNA molecule). Both such homozygous and heterozygous transgenic plants are referred to herein as "progeny plants." Progeny plants are transgenic plants descended from the original transgenic plant which contain the recombinant DNA molecule of the invention. Seeds produced using a transgenic plant of the invention can be harvested and used to grow generations of transgenic plants, i.e., progeny plants, of the invention, comprising the construct of this invention and expressing a gene of agronomic interest. Descriptions of breeding methods that are commonly used for different crops can be found in one of several reference books, see, e.g., Allard, *Principles of Plant Breeding*, John Wiley & Sons, NY, U. of CA, Davis, Calif., 50-98 (1960); Simmonds, *Principles of Crop Improvement*, Longman, Inc., NY, 369-399 (1979); Sneep and Hendriksen, *Plant breeding Perspectives*, Wageningen (ed), Center for Agricultural Publishing and Documentation (1979); Fehr, *Soybeans: Improvement, Production and Uses,* 2nd Edition, Monograph, 16:249 (1987); Fehr, *Principles of Variety Development, Theory and Technique,* (Vol. 1) and *Crop Species Soybean* (Vol. 2), Iowa State Univ., Macmillan Pub. Co., NY, 360-376 (1987).

The transformed plants may be analyzed for the presence of the gene or genes of interest and the expression level and/or profile conferred by the regulatory elements of the invention. Those of skill in the art are aware of the numerous methods available for the analysis of transformed plants. For example, methods for plant analysis include, but are not limited to, Southern blots or northern blots, PCR-based approaches, biochemical analyses, phenotypic screening methods, field evaluations, and immunodiagnostic assays. The expression of a transcribable DNA molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used to evaluate transgene expression.

The invention also provides for parts of a plant of the invention. Plant parts include, but are not limited to, leaves, stems, roots, tubers, seeds, endosperm, ovule, and pollen. Plant parts of the invention may be viable, nonviable, regenerable, and/or non-regenerable. The invention also includes and provides transformed plant cells comprising a DNA molecule of the invention. The transformed or transgenic plant cells of the invention include regenerable and/or non-regenerable plant cells.

The invention may be more readily understood through reference to the following examples, which are provided by way of illustration, and are not intended to be limiting of the invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Identification and Cloning of Regulatory Elements

Novel RCc3 promoters and leaders were identified and cloned from genomic DNA of the monocot species *Coix* (*Coix lacryma-jobi*), Hairy crabgrass (*Digitaria sanguinalis* (L.) Scop.), Maiden grass (*Miscanthus sinensis* f. *gracillimus*), Gama grass (*Tripsacum dactyloides*) and Sugarcane (*Saccharum officinarum*). The RCc3 protein belongs to the prolamin superfamily, which derives its name from the alcohol-souble proline and glutamine rich storage proteins of cereals. The prolamin superfamily (also called protease inhibitor/lipid-transfer protein/seed strorage 2S albumin family; Pfam ID: PF00234) represents one of the most wide-spread protein superfamilies in the plant genome. The members of the prolamin superfamily are abundant in the fruits, nuts, seeds, and vegetables of a variety of plants. They are known to exhibit diverse function including seed storage and protection, lipid binding or transfer, and enzyme inhibition. Lipid transfer proteins (LTPs) belong to the prolamin superfamily and are expressed in a variety of plant tissues. The rice RCc3 protein is an LTP that is expressed in the roots of rice, although not all LTPs proteins are root specific.

DNA amplification primers (presented as SEQ ID NOs: 25-28) were designed using the coding sequences of twenty four (24) LTP proteins from *Zea mays, Oryza sativa, Sorghum bicolor* and *Brachypoium distachyon*. The amplification primers were used with GenomeWalker™ (Clontech Laboratories, Inc, Mountain View, Calif.) libraries constructed following the manufacturer's protocol to clone the 5' region of the corresponding genomic DNA sequence.

Bioinformatic analysis was conducted to identify regulatory elements within the amplified DNA. Using the results of this analysis, regulatory elements were defined within the DNA sequences and primers were designed to amplify the regulatory elements. The corresponding DNA molecule for each regulatory element was amplified using standard polymerase chain reaction (PCR) conditions with primers containing unique restriction enzyme sites and genomic DNA isolated from *C. lacryma-jobi, .D. sanguinalis* (L.) Scop., *M. sinensis* f. *gracillimus, T. dactyloides*, and *S. officinarum*. The resulting DNA fragments were ligated into vectors and sequenced.

The DNA sequences of the identified RCc3 promoters and leaders are listed in Table 1. Promoter sequences are provided herein as SEQ ID NOs: 1, 3, 5, 7, 9, 11, 13, 15, 17, and 19. Leader sequences are provided herein as SEQ ID NOs: 2, 4, 6, 8, 10, 12, 14, 16, 18, and 20.

TABLE 1

RCc3 promoters and leaders isolated from various grass species.

| Sequence Description | SEQ ID NO: | Genus/species |
|---|---|---|
| P-Cl.RCc3:3 | 1 | *Coix lacryma-jobi* |
| L-Cl.RCc3:2 | 2 | *Coix lacryma-jobi* |
| P-Ds.RCc3__1:1 | 3 | *Digitaria sanguinalis* (L.) Scop. |
| L-Ds.RCc3__1:1 | 4 | *Digitaria sanguinalis* (L.) Scop. |
| P-Ds.RCc3__2:1 | 5 | *Digitaria sanguinalis* (L.) Scop. |
| L-Ds.RCc3__2:1 | 6 | *Digitaria sanguinalis* (L.) Scop. |
| P-Ds.RCc3__3:1 | 7 | *Digitaria sanguinalis* (L.) Scop. |
| L-Ds.RCc3__3:1 | 8 | *Digitaria sanguinalis* (L.) Scop. |
| P-MISgr.RCc3__1:1 | 9 | *Miscanthus sinensis* f. *gracillimus* |
| L-MISgr.RCc3__1:1 | 10 | *Miscanthus sinensis* f. *gracillimus* |
| P-MISgr.RCc3-2:2 | 11 | *Miscanthus sinensis* f. *gracillimus* |
| L-MISgr.RCc3-2:1 | 12 | *Miscanthus sinensis* f. *gracillimus* |
| P-Td.RCc3__1:1 | 13 | *Tripsacum dactyloides* |
| L-Td.RCc3__1:1 | 14 | *Tripsacum dactyloides* |
| P-Td.RCc3__2:1 | 15 | *Tripsacum dactyloides* |
| L-Td.RCc3__2:1 | 16 | *Tripsacum dactyloides* |
| P-Td.RCc3__3:1 | 17 | *Tripsacum dactyloides* |
| L-Td.RCc3__3:1 | 18 | *Tripsacum dactyloides* |
| P-So.RCc3:2 | 19 | *Saccharum officinarum* |
| L-So.RCc3:2 | 20 | *Saccharum officinarum* |

Example 2

Analysis of Regulatory Elements Driving GUS in Transgenic Corn

Corn plants were transformed with vectors, specifically binary plasmid constructs, comprising an RCc3 promoter operbably linked to its native RCc3 leader driving expression of the ß-glucuronidase (GUS) transgene. The resulting transformed plants were analyzed for GUS protein expression.

The vectors utilized in these experiments were built using cloning methods known in the art. The resulting vectors comprised a right border region from *A. tumefaciens*; a first transgene expression cassette to assay the RCc3 promoter/leader sequence operably linked to a codon redesigned coding sequence for GUS that possessed a processable intron GOI-Ec.uidA+St.LS1.nno:3 (SEQ ID NO:29) operably linked 5' to the 3' UTR from the foxtail millet S-adenosylmethionine synthetase 1 gene (T-SETit.Ams1-1:1:1, SEQ ID NO:159); a second transgene expression cassette used for selection of transformed plant cells that confers resistance to the herbicide glyphosate (driven by the rice Actin 1 promoter); and a left border region from *A. tumefaciens*. The resulting plasmids were used to transform corn plants using methods known in the art. Expression of GUS conferred by the novel RCc3 promoters and leaders was compared to expression driven by the foxtail millet and rice RCc3 homolog promoters and leaders. Table 2 provides the plasmid constructs, the RCc3 promoter and leader sequences, and the SEQ ID NOs.

TABLE 2

Binary plant transformation plasmids and the associated RCc3 promoter/leader sequences.

| Plasmid Construct | Promoter Sequence Description | SEQ ID NO: | Leader Sequence Description | SEQ ID NO: |
|---|---|---|---|---|
| pMON264146 | P-Cl.RCc3:3 | 1 | L-Cl.RCc3:2 | 2 |
| pMON264148 | P-Ds.RCc3_1:1 | 3 | L-Ds.RCc3_1:1 | 4 |
| pMON264088 | P-Ds.RCc3_2:1 | 5 | L-Ds.RCc3_2:1 | 6 |
| pMON264107 | P-Ds.RCc3_3:1 | 7 | L-Ds.RCc3_3:1 | 8 |
| pMON264186 | P-MISgr.RCc3_1:1 | 9 | L-MISgr.RCc3_1:1 | 10 |
| pMON264187 | P-MISgr.RCc3-2:2 | 11 | L-MISgr.RCc3-2:1 | 12 |
| pMON264049 | P-Td.RCc3_1:1 | 13 | L-Td.RCc3_1:1 | 14 |
| pMON264050 | P-Td.RCc3_2:1 | 15 | L-Td.RCc3_2:1 | 16 |
| pMON264147 | P-Td.RCc3_3:1 | 17 | L-Td.RCc3_3:1 | 18 |
| pMON264166 | P-So.RCc3:2 | 19 | L-So.RCc3:2 | 20 |
| pMON264108 | P-SETit.Rcc3-1:1:10 | 21 | L-SETit.Rcc3-1:1:2 | 22 |
| pMON264206 | P-Os.Rcc3-1:1:24 | 23 | L-Os.Rcc3-1:1:2 | 24 |

In certain instances, plants were transformed using *Agrobacterium*-mediated transformation methods known in the art and as described in U.S. Patent Application Publication 2009/0138985.

Histochemical GUS analysis was used for qualitative expression analysis of the transformed plants. Whole-tissue sections were incubated with GUS staining solution X-Gluc (5-bromo-4-chloro-3-indolyl-b-glucuronide) (1 mg/ml) for an appropriate length of time, rinsed, and visually inspected for blue coloration. GUS activity was qualitatively determined by direct visual inspection or inspection under a microscope using selected plant organs and tissues. The $R_0$ plants were inspected for expression in the roots and leaves, as well as the anther, silk, and developing seed and embryo 21 days after pollination (21 DAP).

For quantitative analysis, total protein was extracted from selected tissues of the transformed corn plants. One microgram of total protein was used with the fluorogenic substrate 4-methyleumbelliferyl-β-D-glucuronide (MUG) in a total reaction volume of 50 microliters. The reaction product, 4-methlyumbelliferone (4-MU), is maximally fluorescent at high pH, where the hydroxyl group is ionized. Addition of a basic solution of sodium carbonate simultaneously stops the assay and adjusts the pH for quantifying the fluorescent product. Fluorescence was measured with excitation at 365 nm, emission at 445 nm, using a Fluoromax-3 (Horiba; Kyoto, Japan) with Micromax Reader, with slit width set at excitation 2 nm, emission 3 nm. The average expression values were provided as pmol 4 MU/µg protein/hour.

The average $R_0$ GUS expression observed for each transformation was recorded and an average expression level and standard error determined based upon the measurements taken of samples derived from multiple transformation events.

Example 3

Enhancers Derived from the Regulatory Elements

Enhancers may be derived from the promoter elements provided herein, such as those presented as SEQ ID NOS: 1, 3, 5, 7, 9, 11, 13, 15, 17, and 19. These enhancer elements may be comprised of one or more cis-regulatory elements that, when operably linked 5' or 3' to a promoter element or operably linked 5' or 3' to additional enhancer elements that are operably linked to a promoter, can enhance or modulate expression of a transcribable DNA molecule, or provide expression of a transcribable DNA molecule in a specific cell type or plant organ, or at a particular time point in development or circadian rhythm. Enhancers are made by removing the TATA box or functionally similar elements and any downstream DNA sequence from the promoters that allow transcription to be initiated from the promoters provided herein as described above, including fragments thereof, in which the TATA box or functionally similar elements and DNA sequence downstream of the TATA box are removed.

Enhancer elements may be derived from the promoter elements provided herein and cloned using methods known in the art to be operably linked 5' or 3' to a promoter element or operably linked 5' or 3' to additional enhancer elements that are operably linked to a promoter. Enhancer elements can be cloned to be operably linked 5' or 3' to a promoter element derived from a different genus organism or operably linked 5' or 3' to additional enhancer elements derived from other genus organisms or the same genus organism that are operably linked to a promoter derived from either the same or different genus organisms, resulting in a chimeric regulatory element. A GUS expression vector may be constructed using methods known in the art similar to the constructs described in the previous Examples in which the resulting plant expression vectors contain a right border region from *A. tumefaciens*; a first transgene cassette to test the regulatory or a chimeric regulatory element comprised of a regulatory or chimeric regulatory element operably linked to an intron derived from the HSP70 heat shock protein of *Z. mays* (I-Zm.DnaK-1:1:1, SEQ ID NO: 38) or any of the introns presented herein or any other intron, operably linked to a coding sequence for GUS that either possesses a processable intron (GUS-2, SEQ ID NO: 32) or no intron (CR-Ec.uidA-1:1:4 (GUS.nat), SEQ ID NO: 31) operably linked to the Nopaline synthase 3' UTR from *A. tumefaciens*

(T-AGRtu.nos-1:1:13, SEQ ID NO: 39) or the 3' UTR from the rice lipid transfer protein gene (T-Os.LTP-1:1:1, SEQ ID NO: 40); a second transgene selection cassette used for selection of transformed plant cells that confers resistance to the herbicide glyphosate (driven by the rice Actin 1 promoter), or alternatively, the antibiotic kanamycin (driven by the rice Actin 1 promoter); and a left border region from *A. tumefaciens*. The resulting plasmids may be used to transform corn plants or other genus plants by the methods described above or by other methods known in the art. Alternatively, protoplast cells derived from corn or other genus plants may be transformed using methods known in the art to perform transient assays.

GUS expression driven by regulatory elements comprising one or more enhancers may be evaluated in stable or transient plant assays to determine the effects of the enhancer element on expression of a transgene. Modifications to one or more enhancer elements or duplication of one or more enhancer elements may be performed based upon empirical experimentation and the resulting gene expression regulation that is observed using each regulatory element composition. Altering the relative positions of one or more enhancers in the resulting regulatory or chimeric regulatory element may affect the transcriptional activity or specificity of the regulatory or chimeric regulatory element and is determined empirically to identify the best enhancers for the desired transgene expression profile within the corn plant or other genus plant.

Example 4

Greater Assay Sensitivity with a Codon-Redesigned ß-Glucuronidase (GUS)

Plant promoters often express at levels that are below the normal detection threshold of many quantitative assays, yet their expression characteristics may be highly valuable for the expression of certain transgenes. In earlier plant biotechnology, promoters that drove high constitititutive expression were desirable and were used to drive transcribable DNA molecules that produced a specific phenotype requiring high constitutive expression, such as herbicide tolerance or insect resistance. These high constitutive promoters were often derived from the genomes of plant viruses rather than plant genomes, for example the 35S promoters derived from Cauliflower mosaic virus and Figwort mosaic virus. Notably, in certain instances, high constitutive expression of certain transcribable DNA molecules may lead to negative consequences such as transgene silencing, off-phenotypes, or yield drag. For example, high expression of the GUS gene in transgenic sugarcane plants using two different sugarcane-derived ubiquitin promoters as well as a maize ubiquitin promoter resulted in post transcriptional gene silencing of the GUS gene (Wei et al., *J Plant Physiol.* 160: 1241-1251, 2003).

Further, recently there is demand for promoters that demonstrate specific patterns of expression or express more highly in specific tissues of the plant. For example, ectopic expression of enzyme genes in plants can result in reduction of the desired end product due to a shortage of precursor at the branching point in a metabolic pathway (Iwase et al., *Plant Biotech.* 26:29-38, 2009). In these instances, it is desirable to use a promoter that expresses the operably linked transcribable DNA molecule in the correct tissue or cell types, or at a particular window of development. Plant genome-derived promoters can often demonstrate desirable tissue, cell, or developmental expression characteristics. Due to the lower expression levels of these plant promoters, expression assays often require the use of enhancers to boost the level of expression to permit detection in a quantitative assay. However, the use of such enhancers often changes the overall expression pattern of the plant promoter.

Improving the expression of the reporter gene used in the assay eliminates the need for enhancement of the plant-derived promoter and, thus, provides a more accurate assessment of the expression pattern conferred by a promoter. This Example demonstrates the use of a codon redesigned GUS coding sequence to improve the quantitative assay sensitivity in characterizing several different EXPs comprised of a promoter sequence, operably linked 5' to a leader sequence, operably linked 5' to a to an intron sequence.

Corn plants were transformed with plant expression vectors containing EXP sequences driving expression of either a native *Escherichia coli* β-glucuronidase (GUS) transgene or codon-redesigned β-glucuronidase (GUS.nno) transgene, and the resulting plants were analyzed for GUS protein expression. The EXP and GUS coding sequences were cloned into binary plasmid constructs using methods known in the art.

Figure 1A:
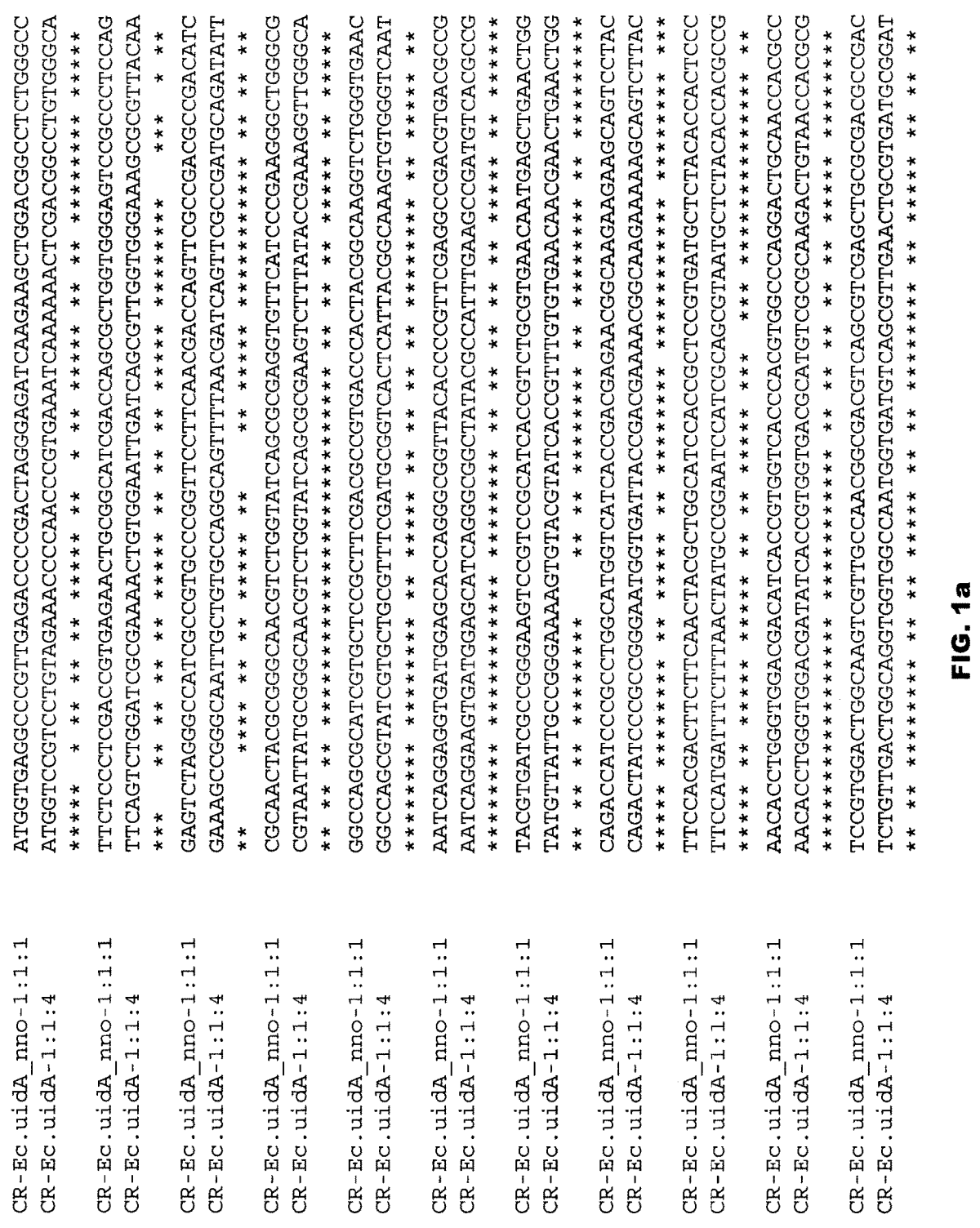

The resulting plant expression constructs contain a right border region from *A. tumefaciens*; a first transgene cassette that demonstrates the assay sensitivity of the two GUS coding sequences, comprised of an EXP operably linked to either a native *E. coli* GUS coding sequence (CR-Ec.uidA-1:1:4 (GUS.nat), SEQ ID NO: 31) or a codon-redesigned GUS coding sequence (CR-Ec.uidA_nno-1:1:1 (GUS.nno), SEQ ID NO: 30) operably linked 5' to the 3' UTR from the rice lipid transfer protein gene (T-Os.LTP-1:1:1, SEQ ID NO: 40); a second transgene selection cassette used for selection of transformed plant cells that confers resistance to the herbicide glyphosate (driven by the rice Actin 1 promoter); and a left border region from *A. tumefaciens*. FIGS. 1a through 1c show an alignment between the native GUS coding sequence (CR-Ec.uidA-1:1:4) and the codon redesigned GUS coding sequence (CR-Ec.uidA_nno-1:1:1). The identical nucleotides in the alignment are indicated by an asterisk. The codon redesigned GUS sequence is 77.9% identical to the native GUS coding sequence and has been designed to express better in the plant.

Three (3) different EXP classes were used, each conferring a specific expression pattern. The EXPs EXP-SETit.Cab3+Zm.DnaK:1:1 (SEQ ID NO: 34) and EXP-SETit.Cab3+Zm.DnaK:1:2 (SEQ ID NO: 35) confer a leaf expression profile in corn and are essentially identical, with the exception of a five-nucleotide insertion of 5'-CCGGA-3' in nucleotide positions 1408 through 1412 of EXP-SETit.Cab3+Zm.DnaK:1:2. The EXP sequence EXP-CaMV.35S-enh+Os.Rcc3+Zm.DnaK:1:5 (SEQ ID NO: 36) provides an enhanced root expression profile in corn. The EXP sequence EXP-Zm.UbqM1:1:2 (SEQ ID NO: 37) provides a high constitutive expression profile in corn. The resulting plasmids were used to transform corn plants using methods known in the art. Table 3 lists the plasmid construct designations, and the corresponding EXP and GUS sequences.

TABLE 3

Plasmid constructs, EXP sequences and expression patterns used to compare native GUS vs. codon-redesigned GUS coding sequences.

| Plasmid Construct | EXP Description | Expression Pattern | SEQ ID NO: | GUS | SEQ ID NO: |
|---|---|---|---|---|---|
| pMON122599 | EXP-SETit.Cab3 + Zm.DnaK:1:2 | Leaf | 35 | CR-Ec.uidA-1:1:4 | 31 |
| pMON122595 | EXP-SETit.Cab3 + Zm.DnaK:1:1 | Leaf | 34 | CR-Ec.uidA_nno-1:1:1 | 30 |
| pMON144050 | EXP-CaMV.35S-enh + Os.Rcc3 + Zm.DnaK:1:5 | Enhanced Root | 36 | CR-Ec.uidA-1:1:4 | 31 |
| pMON122597 | EXP-CaMV.35S-enh + Os.Rcc3 + Zm.DnaK:1:5 | Enhanced Root | 36 | CR-Ec.uidA_nno-1:1:1 | 30 |
| pMON144051 | EXP-Zm.UbqM1:1:2 | Constitutive | 37 | CR-Ec.uidA-1:1:4 | 31 |
| pMON122598 | EXP-Zm.UbqM1:1:2 | Constitutive | 37 | CR-Ec.uidA_nno-1:1:1 | 30 |

In certain instances, plants were transformed using *Agrobacterium*-mediated transformation methods known in the art and as described in U.S. Patent Application Publication 2009/0138985.

Histochemical GUS analysis was used for qualitative expression analysis of the transformed plants. Whole tissue sections were incubated with GUS staining solution X-Gluc (5-bromo-4-chloro-3-indolyl-b-glucuronide) (1 mg/ml) for an appropriate length of time, rinsed, and visually inspected for blue coloration. GUS activity was qualitatively determined by direct visual inspection or inspection under a microscope using selected plant organs and tissues. The R0 plants were inspected for expression in the roots and leaves as well as the anther, silk and developing seed and embryo 21 days after pollination (21 DAP).

For quantitative analysis, total protein was extracted from selected tissues of the transformed corn plants. One microgram of total protein was used with the fluorogenic substrate 4-methyleumbelliferyl-β-D-glucuronide (MUG) in a total reaction volume of 50 µl. The reaction product, 4-methlyumbelliferone (4-MU), is maximally fluorescent at high pH, where the hydroxyl group is ionized. Addition of a basic solution of sodium carbonate simultaneously stops the assay and adjusts the pH for quantifying the fluorescent product. Fluorescence was measured with excitation at 365 nm, emission at 445 nm, using a Fluoromax-3 (Horiba; Kyoto, Japan) with Micromax Reader, with slit width set at excitation 2 nm, emission 3 nm.

The average GUS expression values for the $R_0$ generation transformants are provided in Tables 4, 5, and 6.

TABLE 4

Average $R_0$ generation GUS expression of a native and codon-redesigned GUS coding sequence using an EXP with a leaf expression profile.

| Tissue | pMON122599 EXP-SETit.Cab3 + Zm.DnaK:1:2/ CR-Ec.uidA-1:1:4 | pMON122595 EXP-SETit.Cab3 + Zm.DnaK:1:1/ CR-Ec.uidA_nno-1:1:1 |
|---|---|---|
| V4 Leaf | 798 | 1807 |
| V7 Leaf | 230 | 1863 |
| VT Leaf | 508 | 2097 |
| V4 Root | 0 | 0 |
| V7 Root | 0 | 0 |
| VT Root | 14 | 0 |
| Anther | 95 | 1056 |
| Silk | 154 | 1590 |
| 21 DAP Embryo | 24 | 31 |
| 21 DAP Endosperm | 18 | 61 |

TABLE 5

Average $R_0$ generation GUS expression of a native and codon-redesigned GUS coding sequence using an EXP with an enhanced root expression profile.

| Tissue | pMON144050 EXP-CaMV.35S-enh + Os.Rcc3 + Zm.DnaK:1:5/ CR-Ec.uidA-1:1:4 | pMON122597 EXP-CaMV.35S-enh + Os.Rcc3 + Zm.DnaK:1:5/ CR-Ec.uidA_nno-1:1:1 |
|---|---|---|
| V4 Leaf | 0 | 50 |
| V7 Leaf | 0 | 51 |
| VT Leaf | 0 | 82 |
| V4 Root | 26 | 486 |
| V7 Root | 16 | 257 |
| VT Root | 18 | 343 |
| Anther | 19 | 67 |
| Silk | 0 | 12 |
| 21 DAP Embryo | 14 | 125 |
| 21 DAP Endosperm | 17 | 45 |

TABLE 6

Average $R_0$ generation GUS expression of a native and codon-redesigned GUS coding sequence using an EXP with a constitutive expression profile.

| Tissue | pMON144051 EXP-Zm.UbqM1:1:2/ CR-Ec.uidA-1:1:4 | pMON122598 EXP-Zm.UbqM1:1:2/ CR-Ec.uidA_nno-1 1:1 |
|---|---|---|
| V4 Leaf | 988 | 3327 |
| V7 Leaf | 963 | 2771 |
| VT Leaf | 1777 | 3787 |
| V4 Root | 693 | 2149 |
| V7 Root | 402 | 1443 |
| VT Root | 776 | 3170 |
| Anther | 2247 | 3190 |
| Silk | 975 | 3324 |
| 21 DAP Embryo | 511 | 894 |
| 21 DAP Endosperm | 791 | 2298 |

As can be seen in Tables 4 through 6, there is greater sensitivity in the quantitative assays using the codon-redesigned GUS coding sequence when compared with the native GUS coding sequence. Some variability between the GUS.nno and GUS.nat populations is to be expected, since expression may be affected by insertion sites of the T-DNA; however the overall trend in sensitivity demonstrates much greater sensitivity using GUS.nno. GUS driven by EXP-SETit.Cab3+Zm.DnaK:1:1 (SEQ ID NO: 34) and EXP-SETit.Cab3+Zm.DnaK:1:2 (SEQ ID NO: 35) demonstrated a 2.26- to 8.1-fold greater sensitivity using GUS.nno when compared with GUS.nat. Likewise, the enhanced root profile provided by EXP-CaMV.35S-enh+Os.Rcc3+Zm.DnaK:1:5

(SEQ ID NO: 36) was 16.06- to 19.06-fold greater using GUS.nno than GUS.nat, making this codon-redesigned GUS coding sequence ideal for screening for root promoters, especially those promoters that express at low levels, and may demonstrate GUS levels at or below background levels when using the native GUS coding sequence. The high constitutive expression profile conferred by EXP-Zm.UbqM1:1:2 (SEQ ID NO: 37) demonstrated a 1.42- to 4.09-fold greater quantitative sensitivity when using GUS-.nno compared with GUS.nat.

Qualitatively, GUS staining was more sensitive and consistently observed in tissue samples using the codon-redesigned GUS coding sequence. Generally, qualitative staining observations tend to be less sensitive than quantitative assays. The use of the codon-redesigned GUS coding sequence provides better and more consistent microscopic inspections of stained tissues. For example, in root tissues where GUS was driven by EXP-CaMV.35S-enh+Os.Rcc3+Zm.DnaK:1:5 (SEQ ID NO: 36), histochemical staining of the tissues transformed with the codon-redesigned GUS coding-sequence was more pronounced and visible in all V7 root samples of the cortex, epidermis, endodermis, root hair and secondary root tip. In contrast, GUS staining was not observed qualitatively in the corresponding V7 root tissues when the native GUS coding sequence was driven by EXP-CaMV.35S-enh+Os.Rcc3+Zm.DnaK:1:5. The improved codon-redesigned GUS coding sequence, (CR-Ec.uidA_nno-1:1:1, SEQ ID NO: 30), provided greater assay sensitivity and was particularly valuable in measuring expression of promoters that express at low levels.

Example 5

Analysis of Regulatory Elements Driving GUS in Corn Leaf and Root Protoplasts

Corn leaf and root protoplasts were transformed with vectors comprising an RCc3 promoter operbably linked to its native RCc3 leader driving expression of the ß-glucuronidase (GUS) transgene, and the resulting transformed protoplasts were analyzed for GUS protein expression. The RCc3 promoter and leader sequences were cloned into binary plasmid constructs using methods known in the art and as previously described in Example 2.

Two plasmid constructs for use in co-transformation and normalization of data were also constructed using methods known in the art. Each of these plasmid constructs contained a specific luciferase coding sequence that was driven by a constitutive EXP. The vector pMON19437 comprised a expression cassette with a constitutive promoter operably linked 5' to an intron, (EXP-CaMV.35S-enh+Zm.DnaK:1, SEQ ID NO: 41), operably linked 5' to a firefly (*Photinus pyralis*) luciferase coding sequence (LUCIFERASE:1:3, SEQ ID NO: 42), operably linked 5' to a 3' UTR from the *Agrobacterium tumefaciens* nopaline synthase gene (T-AGRtu.nos-1:1:13, SEQ ID NO: 39). The vector pMON63934 comprised an expression cassette with a constitutive EXP sequence (EXP-CaMV.35S-enh-Lhcb1, SEQ ID NO: 44) operably linked 5' to a sea pansy (*Renilla reniformis*) luciferase coding sequence (CR-Ren.hRenilla Lucife-0:0:1, SEQ ID NO: 43), operably linked 5' to a 3' UTR from the *Agrobacterium tumefaciens* nopaline synthase gene (T-AGRtu.nos-1:1:13, SEQ ID NO: 39).

Corn root and leaf protoplasts were transformed using a polyethylene glycol (PEG)-based transformation method, which is well known in the art. Protoplast cells were transformed with pMON19437, pMON63934, and one of the plasmids presented in Table 7. After transformation, the transformed protoplasts were incubated overnight in total darkness. Next, measurement of both GUS and luciferase were conducted by placing aliquots of a lysed preparation of cells transformed as noted above into two different small-well trays. One tray was used for GUS measurements and a second tray was used to perform a dual luciferase assay using the dual luciferase reporter assay system (Promega Corp., Madison, Wis.; see e.g., Promega Notes Magazine, No: 57, 1996, p. 02).

Four transformations for each EXP or promoter+ leader+ intron sequence were performed. The mean expression values for each EXP or promoter+ leader+ intron sequence were determined from several samples from each transformation. Sample measurements were made using four replicates of each EXP or promoter+ leader+ intron sequence plasmid construct transformation. Background GUS expression was determined using a negative control plasmid construct which lacked the GUS transgene. The average GUS and luciferase expression levels are provided in Tables 7 (leaf) and 8 (root). In these tables, the firefly luciferase values (e.g., from expression of pMON19437) are provided in the column labeled "FLUC" and the sea pansy luciferase values (e.g., from expression of pMON63934) are provided as in the column labeled "RLUC." Also provided in Tables 7 and 8 are the average GUS/FLUC and GUS/RLUC ratios which provide a relative measure of expression strength in the protoplast assays.

TABLE 7

Average GUS, FLUC and RLUC values derived from transformed corn leaf protoplasts.

| Plasmid Construct | Promoter Leader | SEQ ID NO: | Average GUS | Average FLUC | Average RLUC | Average GUS/FLUC | Average GUS/RLUC |
|---|---|---|---|---|---|---|---|
| pMON264146 | P-Cl.RCc3:3 | 1 | 5328064.75 | 105434 | 253107.5 | 50.73 | 21.15 |
|  | L-Cl.RCc3:2 | 2 |  |  |  |  |  |
| pMON264148 | P-Ds.RCc3_1:1 | 3 | 773613 | 147918 | 338149.5 | 5.23 | 2.28 |
|  | L-Ds.RCc3_1:1 | 4 |  |  |  |  |  |
| pMON264088 | P-Ds.RCc3_2:1 | 5 | 2883555.75 | 129947.5 | 309268.5 | 22.33 | 9.45 |
|  | L-Ds.RCc3_2:1 | 6 |  |  |  |  |  |
| pMON264107 | P-Ds.RCc3_3:1 | 7 | 1093785 | 124864.75 | 306178.75 | 8.70 | 3.55 |
|  | L-Ds.RCc3_3:1 | 8 |  |  |  |  |  |
| pMON264186 | P-MISgr.RCc3_1:1 | 9 | 2613839.75 | 128887.25 | 301412.75 | 20.45 | 8.83 |
|  | L-MISgr.RCc3_1:1 | 10 |  |  |  |  |  |
| pMON264187 | P-MISgr.RCc3-2:2 | 11 | 2370706.25 | 149383.5 | 370443.75 | 15.95 | 6.53 |
|  | L-MISgr.RCc3-2:1 | 12 |  |  |  |  |  |

TABLE 7-continued

Average GUS, FLUC and RLUC values derived from transformed corn leaf protoplasts.

| Plasmid Construct | Promoter Leader | SEQ ID NO: | Average GUS | Average FLUC | Average RLUC | Average GUS/FLUC | Average GUS/RLUC |
|---|---|---|---|---|---|---|---|
| pMON264049 | P-Td.RCc3__1:1 | 13 | 7506585.75 | 150939.25 | 368035.5 | 50.15 | 20.88 |
| | L-Td.RCc3__1:1 | 14 | | | | | |
| pMON264050 | P-Td.RCc3__2:1 | 15 | 4447254.25 | 155356.25 | 364604.5 | 28.78 | 12.40 |
| | L-Td.RCc3__2:1 | 16 | | | | | |
| pMON264147 | P-Td.RCc3__3:1 | 17 | 1100118.75 | 153451 | 316691.5 | 7.13 | 3.48 |
| | L-Td.RCc3__3:1 | 18 | | | | | |
| pMON264166 | P-So.RCc3:2 | 19 | 3062045 | 143684.5 | 332394.5 | 21.55 | 9.45 |
| | L-So.RCc3:2 | 20 | | | | | |
| pMON264108 | P-SETit.Rcc3-1:1:10 | 21 | 147483 | 129834.25 | 300917.25 | 1.15 | 0.50 |
| | L-SETit.Rcc3-1:1:2 | 22 | | | | | |
| pMON264206 | P-Os.Rcc3-1:1:24 | 23 | 184905.25 | 171440.75 | 386387.25 | 1.08 | 0.50 |
| | L-Os.Rcc3-1:1:2 | 24 | | | | | |

TABLE 8

Average GUS, FLUC and RLUC values derived from transformed corn root protoplasts.

| Plasmid Construct | Promoter Leader | SEQ ID NO: | Average GUS | Average FLUC | Average RLUC | Average GUS/FLUC | Average GUS/RLUC |
|---|---|---|---|---|---|---|---|
| pMON264146 | P-Cl.RCc3:3 | 1 | 185142.3 | 18310 | 34502.5 | 10.18 | 5.43 |
| | L-Cl.RCc3:2 | 2 | | | | | |
| pMON264148 | P-Ds.RCc3__1:1 | 3 | 16306.5 | 17008 | 31233 | 0.98 | 0.53 |
| | L-Ds.RCc3__1:1 | 4 | | | | | |
| pMON264088 | P-Ds.RCc3__2:1 | 5 | 101603.8 | 19201.25 | 43298 | 5.23 | 2.33 |
| | L-Ds.RCc3__2:1 | 6 | | | | | |
| pMON264107 | P-Ds.RCc3__3:1 | 7 | 29196 | 14483.5 | 34700.75 | 2.03 | 0.88 |
| | L-Ds.RCc3__3:1 | 8 | | | | | |
| pMON264186 | P-MISgr.RCc3__1:1 | 9 | 87232 | 18411.75 | 44755.75 | 4.80 | 1.95 |
| | L-MISgr.RCc3__1:1 | 10 | | | | | |
| pMON264187 | P-MISgr.RCc3-2:2 | 11 | 510761.5 | 19093.75 | 41948.5 | 26.98 | 12.30 |
| | L-MISgr.RCc3-2:1 | 12 | | | | | |
| pMON264049 | P-Td.RCc3__1:1 | 13 | 884517.8 | 23881.75 | 55790 | 37.23 | 16.18 |
| | L-Td.RCc3__1:1 | 14 | | | | | |
| pMON264050 | P-Td.RCc3__2:1 | 15 | 91634.5 | 18385 | 43509.5 | 5.03 | 2.18 |
| | L-Td.RCc3__2:1 | 16 | | | | | |
| pMON264147 | P-Td.RCc3__3:1 | 17 | 50257.25 | 18716.75 | 34489 | 2.65 | 1.45 |
| | L-Td.RCc3__3:1 | 18 | | | | | |
| pMON264166 | P-So.RCc3:2 | 19 | 508345.3 | 22335.25 | 51655.75 | 22.98 | 10.13 |
| | L-So.RCc3:2 | 20 | | | | | |
| pMON264108 | P-SETit.Rcc3-1:1:10 | 21 | 8123 | 17750.75 | 37872.25 | 0.45 | 0.23 |
| | L-SETit.Rcc3-1:1:2 | 22 | | | | | |
| pMON264206 | P-Os.Rcc3-1:1:24 | 23 | 336095.3 | 17709.5 | 40179.5 | 19.65 | 8.63 |
| | L-Os.Rcc3-1:1:2 | 24 | | | | | |

As demonstrated in Table 7, all of the RCc3 homolog promoters demonstrated the ability to drive transgene expression in corn leaf protoplasts. Some of the RCc3 homolog promoters drove expression higher than others in this assay based upon the GUS/FLUC and GUS/RLUC ratios. Further, as demonstrated in Table 8 above, all of the RCc3 homolog promoters demonstrated the ability to drive transgene expression in corn root protoplasts to varying degrees.

Example 6

Analysis of Regulatory Elements Driving GUS in Transgenic Corn

Corn plants were transformed with vectors comprising an RCc3 promoter operbably linked to its native RCc3 leader driving expression of the ß-glucuronidase (GUS) transgene. The resulting transformed plants were analyzed for GUS protein expression.

The RCc3 promoter and leader sequences were cloned into binary plasmid constructs using methods known in the art, such as those described in Example 2. The resulting binary plasmid constructs were pMON264146, pMON264148, pMON264088, pMON264107, pMON264186, pMON264187, pMON264049, pMON264050, pMON264147 and pMON264166. The corn plants were also stably transformed with pMON264108 and pMON264206. Qualitative and quantitative GUS expression analysis was performed as described in Example 2. The plants were assayed at V4, V7 and VT stage of development. Sampling at R1 and R3 is shown. Table 9 shows the average quantitative GUS expression for stably transformed corn plants.

TABLE 9

Average quantitative GUS expression in stably transformed corn plants.

| Plasmid Construct | Promoter Leader | SEQ ID NO: | V4 Leaf | V4 Root | V7 Leaf | V7 Root | VT Leaf | VT Root | VT Flower/ anthers | R1 Cob/silk | R3 21DAP Embryo | R3 21DAP Endosperm |
|---|---|---|---|---|---|---|---|---|---|---|---|---|
| pMON264146 | P-Cl.RCc3:3<br>L-Cl.RCc3:2 | 1<br>2 | 25.15 | 61.31 | 20.71 | 42.64 | 35.96 | 95.19 | 298 | 125.12 | 21.97 | 186.52 |
| pMON264148 | P-Ds.RCc3_1:1<br>L-Ds.RCc3_1:1 | 3<br>4 | 48.34 | 36.81 | 42.49 | 125.25 | 69.76 | 55.44 | 277.93 | 58 | 67.08 | 115.71 |
| pMON264088 | P-Ds.RCc3_2:1<br>L-Ds.RCc3_2:1 | 5<br>6 | 28.31 | 51.18 | 59.2 | 149.2 | 70.93 | 158.32 | 214.47 | 120.72 | 141.85 | 164.68 |
| pMON264107 | P-Ds.RCc3_3:1<br>L-Ds.RCc3_3:1 | 7<br>8 | 67.1 | 327.44 | 85.02 | 365.51 | 161.65 | 202.17 | 787.25 | 103.63 | | |
| pMON264186 | P-MISgr.RCc3_1:1<br>L-MISgr.RCc3_1:1 | 9<br>10 | 38.66 | 40.25 | 39.7 | 139.98 | 105.24 | 308.24 | 406.38 | 239.35 | 118.54 | 196.48 |
| pMON264187 | P-MISgr.RCc3-2:2<br>L-MISgr.RCc3-2:1 | 11<br>12 | 25.9 | 193.25 | 42.13 | 291.5 | 48.02 | 549.37 | 87.89 | 41.83 | | |
| pMON264049 | P-Td.RCc3_1:1<br>L-Td.RCc3_1:1 | 13<br>14 | 283.86 | 238.31 | | | | | | | | |
| pMON264050 | P-Td.RCc3_2:1<br>L-Td.RCc3_2:1 | 15<br>16 | 51.82 | 653.38 | | | | | | | | |
| pMON264147 | P-Td.RCc3_3:1<br>L-Td.RCc3_3:1 | 17<br>18 | 42.49 | 55.87 | 41.49 | 197.51 | 117.77 | 282.63 | 1182.96 | 938.3 | 815.36 | 1240.92 |
| pMON264166 | P-So.RCc3:2<br>L-So.RCc3:2 | 19<br>20 | 34.11 | 215.86 | 125.91 | 855.23 | 79.33 | 237.25 | 347.99 | 177.13 | | |

As demonstrated in Table 9, all of the RCc3 promoter homologs were able to drive GUS transgene expression in stably transformed corn plants. Further, each promoter had a pattern of expression that was unique to the specific promoter. For example, expression in VT flower/anther differed amongst the RCc3 promoter homologs. Expression driven by P-Td.RCc3_3:1 (SEQ ID NO: 17) was the highest expression observed for all the promoters, while expression driven by P-MISgr.RCc3-2:2 (SEQ ID NO: 11) was the lowest. With respect to R1 Cob/silk expression, P-Td.RCc3_3:1 (SEQ ID NO: 17) demonstrated the highest expression in these tissues and P-MISgr.RCc3-2:2 (SEQ ID NO: 11) expressed the least. Expression driven by P-Td.RCc3_3:1 (SEQ ID NO: 17) increased in later developing tissues. Expression increased in the root from V4 to VT stage and was even higher in VT flowers/anthers, R1 Cob/silk and R3 21DAP embryo and endosperm. Expression driven by P-Td.RCc3_3:1 was highest amongst the RCc3 promoter homologs in VT flowers/anthers, R1 Cob/silk, and R3 21DAP embryo and endosperm.

With respect to leaf and root expression, some of the RCc3 promoter homologs demonstrated higher expression in the root relative to the leaf. Table 10 shows the root-to-leaf expression ratios for all of assayed RCc3 promoters.

TABLE 10

Root/Leaf expression ratios for stably transformed corn plants.

| Plasmid Construct | Promoter Leader | SEQ ID NO: | Average Root/Leaf V4 | V7 | VT |
|---|---|---|---|---|---|
| pMON264146 | P-Cl.RCc3:3<br>L-Cl.RCc3:2 | 1<br>2 | 2.44 | 2.06 | 2.65 |
| pMON264148 | P-Ds.RCc3_1:1<br>L-Ds.RCc3_1:1 | 3<br>4 | 0.76 | 2.95 | 0.79 |
| pMON264088 | P-Ds.RCc3_2:1<br>L-Ds.RCc3_2:1 | 5<br>6 | 1.81 | 2.52 | 2.23 |
| pMON264107 | P-Ds.RCc3_3:1<br>L-Ds.RCc3_3:1 | 7<br>8 | 4.88 | 4.30 | 1.25 |
| pMON264186 | P-MISgr.RCc3_1:1<br>L-MISgr.RCc3_1:1 | 9<br>10 | 1.04 | 3.53 | 2.93 |
| pMON264187 | P-MISgr.RCc3-2:2<br>L-MISgr.RCc3-2:1 | 11<br>12 | 7.46 | 6.92 | 11.44 |
| pMON264049 | P-Td.RCc3_1:1<br>L-Td.RCc3_1:1 | 13<br>14 | 0.84 | | |
| pMON264050 | P-Td.RCc3_2:1<br>L-Td.RCc3_2:1 | 15<br>16 | 12.61 | | |
| pMON264147 | P-Td.RCc3_3:1<br>L-Td.RCc3_3:1 | 17<br>18 | 1.31 | 4.76 | 2.40 |
| pMON264166 | P-So.RCc3:2<br>L-So.RCc3:2 | 19<br>20 | 6.33 | 6.79 | 2.99 |

As demonstrated in Table 10, each RCc3 promoter homolog demonstrated different ratios of root-to-leaf expression and different patters from V4 to VT stage. For example, P-Cl.RCc3:3 (SEQ ID NO: 1) maintained a similar ratio of expression from V4 through VT with a slight decline occurring at V7 stage. Expression in the root as seen in Table 9 dropped slightly from V4 to V7 and then increased by VT stage. The promoter P-Ds.RCc3_3:1 (SEQ ID NO: 7) demonstrated a change in expression ratios from V4 through VT stage with higher expression in the root relative to the leaf in V4 and V7 stage and then a shift approximating equal expression in the leaf relative to the root at VT stage (1.25). With this promoter the average expression shown in Table 9 demonstrates an increase in expression in the leaf from V4 to VT stage while expression in the root declined from V7 to VT stage. The promoter P-So.RCc3:2 (SEQ ID NO: 19) maintained a ratio of root-to-leaf expression of 6.33 at V4 and 6.79 at V7 stage, but then dropped to 2.99 at VT stage. However, expression with this promoter increased 3.69 and 3.96 fold in the leaf and root, respectively, from V4 to V7 stage and then decreased to 2.33 and 1.10 relative to V4 at VT stage.

Notably, not all promoters had a higher root-to-leaf ratio. For example, the promoters P-Ds.RCc3_1:1 (SEQ ID NO: 3) and P-Td.RCc3_1:1 (SEQ ID NO: 13) had root/leaf ratios less than one at V4 stage. However, expression driven by P-Td.RCc3_1:1 was 6.6 fold greater than P-Ds.RCc3_1:1 in V4 root. The highest ratio of root/leaf at V4 stage was achieved using P-Td.RCc3_2:1 (SEQ ID NO: 15). The ratio of root/leaf expression driven by P-Ds.RCc3_1:1 increased from V4 (0.76) to V7 (2.95) and then returned to a ratio similar to that at V4 (0.79).

The promoter P-MISgr.RCc3-2:2 (SEQ ID NO: 11) demonstrated an increase in expression in both leaf and root from V4 to VT stage. This promoter had a root-to-leaf ratio greater than 6.9 throughout all three stages, but the ratio went from 7.46 at V4 stage to 6.92 at V7 stage and then climbed to 11.44 at VT stage. Expression driven by P-MISgr.RCc3-2:2 increased in the leaf and root from V4 to VT stage.

Each of the RCc3 homolog promoters demonstrated patterns of expression in stably transformed corn that could not necessarily be predicted by virtue of being derived from homologous genes, especially when used to transform a heterologous species such as corn. Most of the promoters demonstrated higher expression in the root with respect to the leaf at some point either in V4, V7 or VT stage or in all stages assayed. Notably, the magnitude of expression differed extensively between the promoters. The unique expression properties of each of the RCc3 promoter homologs make some more suitable than others for certain types of transcribable DNA molecule expression. For example, expression of a transcribable DNA molecule that may be critical to the assimilation of a nutrient in the soil and which is best expressed at a later stage of development when the plant is about to begin reproduction and produce seed, may benefit best from a promoter such as P-MISgr.RCc3-2:2 (SEQ ID NO: 11) which increases expression in the root around VT stage.

Having illustrated and described the principles of the invention, it should be apparent to persons skilled in the art that the invention can be modified in arrangement and detail without departing from such principles. We claim all modifications that are within the spirit and scope of the claims. All publications and published patent documents cited herein are hereby incorporated by reference to the same extent as if each individual publication or patent application is specifically and individually indicated to be incorporated by reference.

What is claimed is:

1. A recombinant DNA molecule comprising a DNA sequence selected from the group consisting of:
    a) a DNA sequence with at least 99 percent sequence identity to the full length of SEQ ID NO: 15, wherein the sequence has gene-regulatory activity;
    b) a DNA sequence comprising SEQ ID NO: 15; and
    c) a fragment comprising at least 600 contiguous nucleotides of SEQ ID NO: 15, wherein the fragment has gene-regulatory activity;
    wherein said sequence is operably linked to a heterologous transcribable polynucleotide molecule.

2. The recombinant DNA molecule of claim 1, wherein the heterologous transcribable DNA molecule comprises a gene of agronomic interest.

3. The recombinant DNA molecule of claim 2, wherein the gene of agronomic interest confers herbicide tolerance in plants.

4. The recombinant DNA molecule of claim 2, wherein the gene of agronomic interest confers pest resistance in plants.

5. A transgenic plant cell comprising a recombinant DNA molecule comprising a DNA sequence selected from the group consisting of:
    a) a DNA sequence with at least 99 percent sequence identity to the full length of SEQ ID NO: 15, wherein the sequence has gene-regulatory activity;
    b) a DNA sequence comprising SEQ ID NO: 15; and
    c) a fragment comprising at least 600 contiguous nucleotides of SEQ ID NO: 15, wherein the fragment has gene-regulatory activity;
    wherein said sequence is operably linked to a heterologous transcribable polynucleotide molecule.

6. The transgenic plant cell of claim 5, wherein said transgenic plant cell is a monocotyledonous plant cell.

7. The transgenic plant cell of claim 5, wherein said transgenic plant cell is a dicotyledonous plant cell.

8. A transgenic plant, or part thereof, comprising a recombinant DNA molecule comprising a DNA sequence selected from the group consisting of:
    a) a DNA sequence with at least 95 99 percent sequence identity to the full length of SEQ ID NO: 15, wherein the sequence has gene-regulatory activity;
    b) a DNA sequence comprising SEQ ID NO: 15; and
    c) a fragment comprising at least 500 600 contiguous nucleotides of SEQ ID NO: 15, wherein the fragment has gene-regulatory activity;
    wherein said sequence is operably linked to a heterologous transcribable polynucleotide molecule.

9. A progeny plant of the transgenic plant of claim 8, or a part thereof, wherein the progeny plant or part thereof comprises said recombinant DNA molecule.

10. A transgenic seed of the transgenic plant of claim 8, wherein the seed comprises the recombinant DNA molecule.

11. A method of producing a commodity product comprising obtaining a transgenic plant or part thereof according to claim 8 and producing the commodity product therefrom.

12. The method of claim 11, wherein the commodity product is processed seeds, grains, plant parts, and meal.

13. A method of producing a transgenic plant comprising:
    a) transforming a plant cell with the recombinant DNA molecule of claim 1 to produce a transformed plant cell; and
    b) regenerating a transgenic plant from the transformed plant cell.

14. The recombinant DNA molecule of claim 1, wherein the DNA sequence has at least 99 percent sequence identity to the full length of SEQ ID NO: 15, and wherein the sequence has gene-regulatory activity.

15. The recombinant DNA molecule of claim 1, wherein the DNA sequence comprises SEQ ID NO: 15.

16. The recombinant DNA molecule of claim 1, wherein the DNA sequence comprises the fragment comprising at least 600 contiguous nucleotides of SEQ ID NO: 15, and wherein the fragment has gene-regulatory activity.

* * * * *